(12) United States Patent
Cummings et al.

(10) Patent No.: US 7,005,301 B2
(45) Date of Patent: Feb. 28, 2006

(54) PIECEWISE UNIFORM CONDUCTION-LIKE FLOW CHANNELS AND METHOD THEREFOR

(75) Inventors: Eric B. Cummings, Livermore, CA (US); Gregory J. Fiechtner, Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 336 days.

(21) Appl. No.: 10/456,772

(22) Filed: Jun. 6, 2003

(65) Prior Publication Data
US 2003/0230489 A1 Dec. 18, 2003

Related U.S. Application Data

(60) Provisional application No. 60/387,684, filed on Jun. 10, 2002.

(51) Int. Cl.
*B01L 3/02* (2006.01)
(52) U.S. Cl. ...................................... 436/180; 422/100
(58) Field of Classification Search ................ 422/99, 422/100, 102, 81; 436/180, 174
See application file for complete search history.

(56) References Cited

U.S. PATENT DOCUMENTS

| | | | | |
|---|---|---|---|---|
| 5,486,335 A | * | 1/1996 | Wilding et al. | 422/55 |
| 5,842,787 A | * | 12/1998 | Kopf-Sill et al. | 366/340 |
| 5,852,495 A | * | 12/1998 | Parce | 356/344 |
| 6,176,991 B1 | * | 1/2001 | Nordman | 204/601 |
| 6,270,641 B1 | * | 8/2001 | Griffiths et al. | 204/451 |
| 6,368,871 B1 | * | 4/2002 | Christel et al. | 436/180 |
| 6,451,264 B1 | * | 9/2002 | Bhullar et al. | 422/100 |
| 6,517,234 B1 | * | 2/2003 | Kopf-Sill et al. | 366/340 |
| 6,733,730 B1 | * | 5/2004 | Griffiths et al. | 422/100 |
| 6,802,640 B1 | * | 10/2004 | Schubert et al. | 366/181.6 |

* cited by examiner

*Primary Examiner*—Jeffrey R. Snay
(74) *Attorney, Agent, or Firm*—Timothy P. Evans

(57) ABSTRACT

A low-dispersion methodology for designing microfabricated conduction channels for on-chip electrokinetic-based systems is presented. The technique relies on trigonometric relations that apply for ideal electrokinetic flows, allowing faceted channels to be designed on chips using common drafting software and a hand calculator. Flows are rotated and stretched along the abrupt interface between adjacent regions with differing permeability. Regions bounded by interfaces form flow "prisms" that can be combined with other designed prisms to obtain a wide range of turning angles and expansion ratios while minimizing dispersion. Designs are demonstrated using two-dimensional numerical solutions of the Laplace equation.

55 Claims, 41 Drawing Sheets

1
_____
2
_____
FIG. 25A
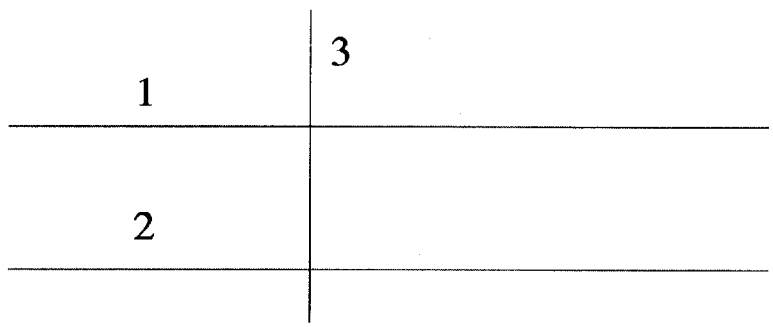
FIG. 25B
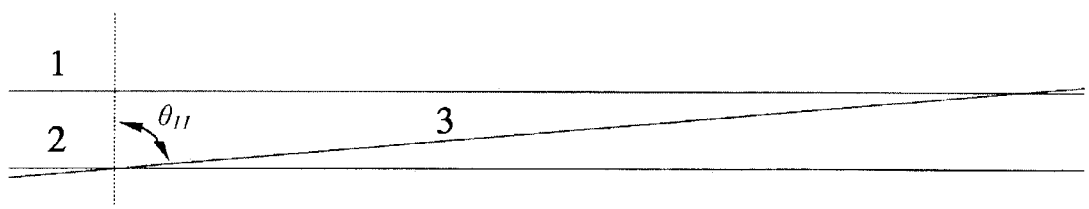
FIG. 25C

PIECEWISE UNIFORM CONDUCTION-LIKE FLOW CHANNELS AND METHOD THEREFOR

CROSS REFERENCE TO RELATED APPLICATIONS

This application claims priority to, prior co-pending provisional U.S. Patent Application Ser. No. 60/387,684 originally filed Jun. 10, 2002 entitled "METHOD FOR PROVIDING CONDUCTION-LIKE FLOW CHANNELS AND APPLICATION THEREFOR" from which benefit is claimed.

STATEMENT OF GOVERNMENT INTEREST

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

BACKGROUND OF THE INVENTION

Many engineering functions and/or analytical processes require moving a fluid. These tasks are increasingly utilizing systems that rely on one or more fluid channels having cross-sectional dimensions ranging from a few thousand to a few tens of microns across. Moreover, there is a drive to provide large-scale integration of multiple fluid handling features on a single substrate ("chip") in a manner analogous to that in microelectronics.

Most, if not all, of these applications seek to minimize the non-uniformity present to a greater or lesser extent in all fluid handling systems. This non-uniformity results in unintended and undesirable hydrodynamic dispersion and stagnation.

A primary source of non-uniform fluid flow derives from the drag imposed on the fluid at fluid/channel interfaces, and by secondary effects such as eddying. The use of electrokinetics to transport liquids mitigates these sources of dispersion, but non-uniform flow persists even when using electrokinetic transport due to non-uniform electric fields that arise in the fluid where the flow changes direction, or "turns," at corners or junctions in a channel manifold. Furthermore, these effects are exaggerated as the aspect ratio of the flow channel decreases such that shallow and wide flow channels, which are the most readily fabricated, are the most affected.

What is needed, therefore, is a method for controlling or eliminating non-uniform fluid flow in flow channels, especially in microchannel systems. For example, a method for reducing or eliminating hydrodynamic dispersion in flow channels is sought. Moreover, there is a need for controlling hydrodynamic dispersion in fluids moving in a fluid system as the flow is turned, split, combined, and/or expanded at junctions, corners, "tees," or branches in a system manifold.

Two different approaches have been used in previous efforts to minimize the dispersion induced by turns and by contractions at the ends of separation channels. Kopf-Sill, et al., and Parce (U.S. Pat. Nos. 5,842,787 and 5,852,495) teach to reduce dispersion by the use of specific channel geometries. In particular, they recommend channels having large aspect ratios such that the channel depths are much greater than their widths. The smaller channel width helps to reduce the difference in transit time along the inner and outer walls of a turn, thereby reducing dispersion. It is also suggested that dispersion can be reduced by fabrication of turns having a depth along the inner radius that is greater than that along the outer radius, thereby reducing the fluid speed along the inner radius. Griffiths, et al., (U.S. Pat. No. 6,270,641) teach the use of geometry to reduce dispersion, particularly by providing contraction and expansion regions at junctions and corners that reduce the cross-sectional area over some portion of the turn or junction. By carefully designing the geometries of these regions, sample dispersion in turns and junctions is reduced to levels comparable to the effects of ordinary diffusion.

SUMMARY OF THE INVENTION

The present invention improves the performance of microchannel systems by changing the conductance or permeability, and the size and shape of the channel in the region of the desired junctions so that the flow is piece-wise uniform. By carefully designing the geometries of low and high permeability regions in the channel, dispersion produced by the junctions is essentially eliminated. Embodiments of the invention include: turns of any angle, splitters, combiners, and expanders.

For the purposes of the present invention, flow channels are defined as structures comprising substantially parallel top and bottom interior surfaces and interior side walls separating the top and bottom surfaces and generally parallel to a longitudinal axis running the length of the channel. Moreover, the present invention comprehends a design methodology for assembling structures comprising two or more channel lengths which intersect to form a segmented group, or "chain" of channels, wherein corresponding side walls of adjacent channels meet at the intersection plane, and wherein these intersecting channel lengths are aligned to rotate a fluid through a predetermined turn angle. This design methodology will also show that any or all of the intersecting channel lengths may also comprise a side wall that has been reduced to an infinitesimal length to provide for an intermediate channel segments having the shape of a faceted triangle.

This invention is applicable to pressure-driven chromatographic separations, electrochromatographic separations and electrophoretic separations, as well as many microfluidic processes such as routine sample transport, sample mixing, sample reaction and species synthesis. It is also applicable to channels and junctions that are open, filled with a gel, or filled with a porous or granular material. Moreover, the technique is applicable to designs of piece-wise uniform electrical and thermal conduction channels.

In one embodiment, the improved turns and junctions consist of channel regions having piece-wise uniform depths, permitting straightforward fabrication by conventional etching, molding and embossing techniques. Further, because the turns and junctions are only moderately constricted over relatively short distances, they do not lead to excessive increases in Joule heating.

BRIEF DESCRIPTION OF TALE DRAWINGS

FIGS. 1A–D illustrate methods of modifying the conductance/permeability of a conduction channel.

FIG. 2 Sketch of the one-dimensional conduction channel. The conductance or permeability, $\sigma$, is constant in regions 1 and 2 and varies only in the flow direction in the transition region, $\nabla \sigma \times u \equiv 0$;

FIG. 3 Sketch of the one-dimensional conduction channel from the standpoint of an observer moving with velocity $u_o$ along the interface. The velocities $u_{1o}$ and $u_{2o}$ are shown in this frame.

Figure 6A:
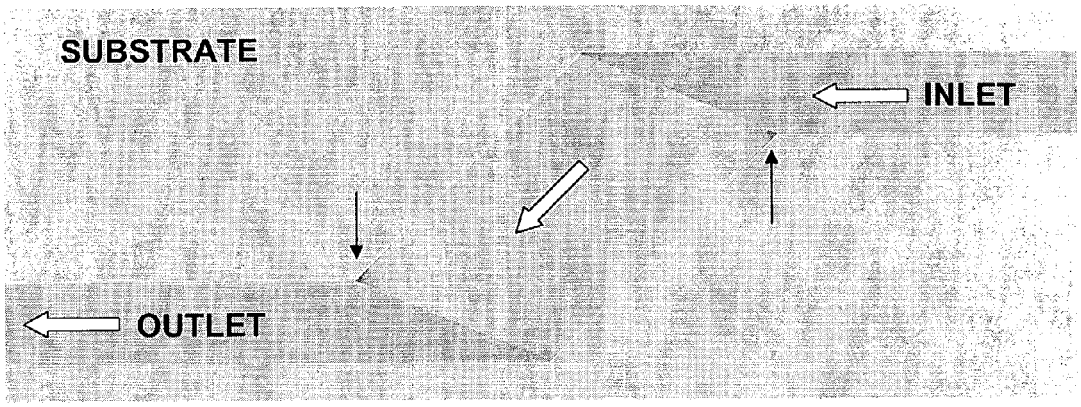
Figure 6B:
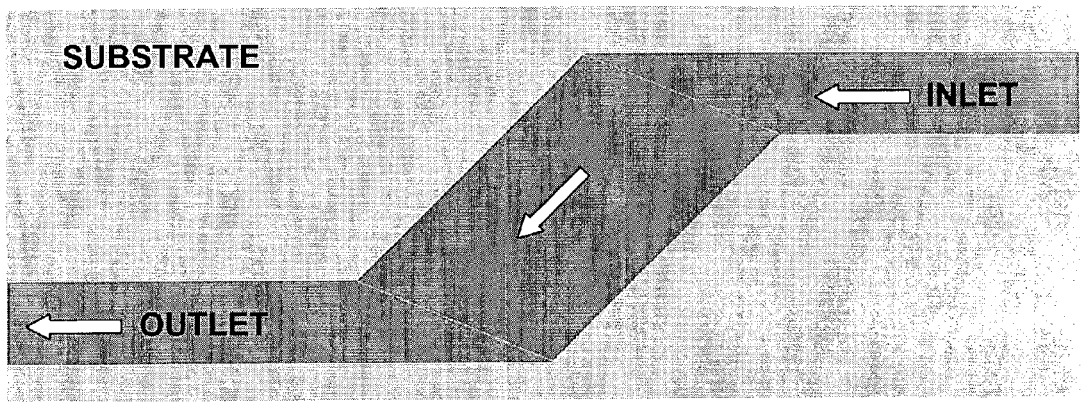
Figure 6C:
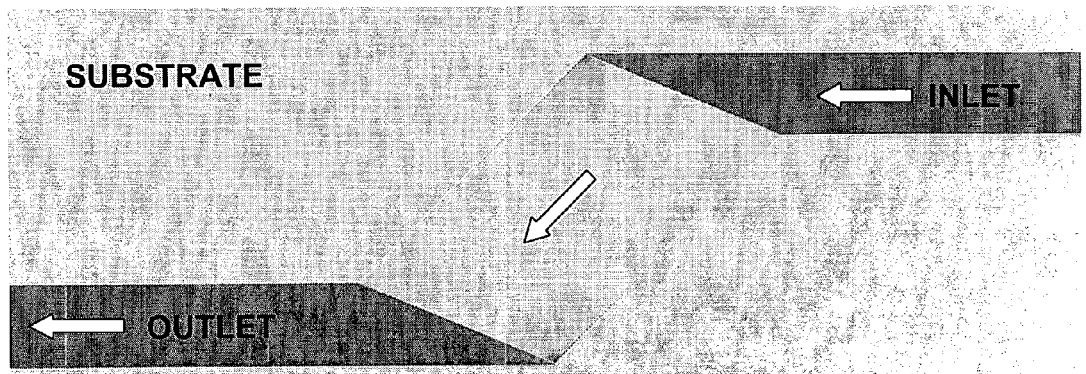

FIGS. 6A–C show numerical simulations of the speed field for three examples of a system with two interfaces.

Figure 7A:
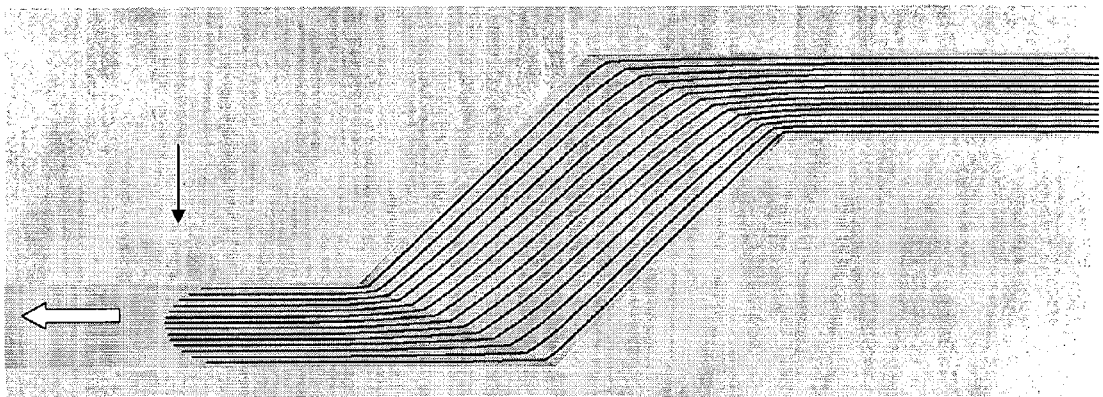
Figure 7B:
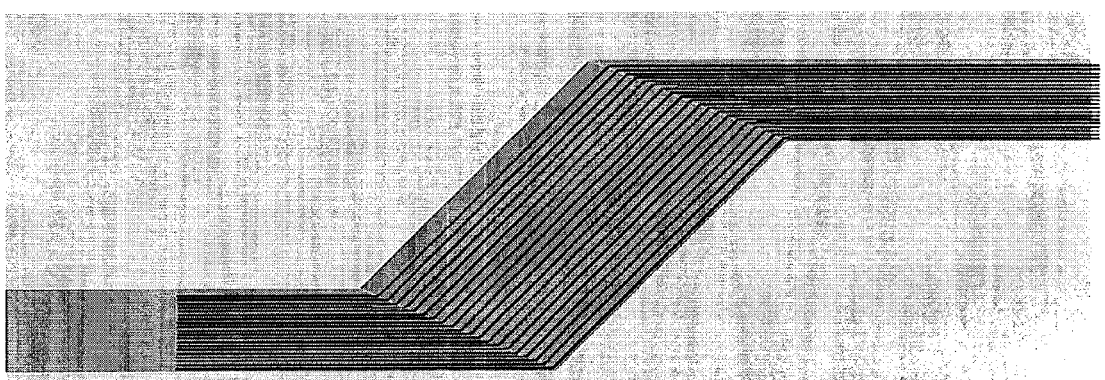
Figure 7C:
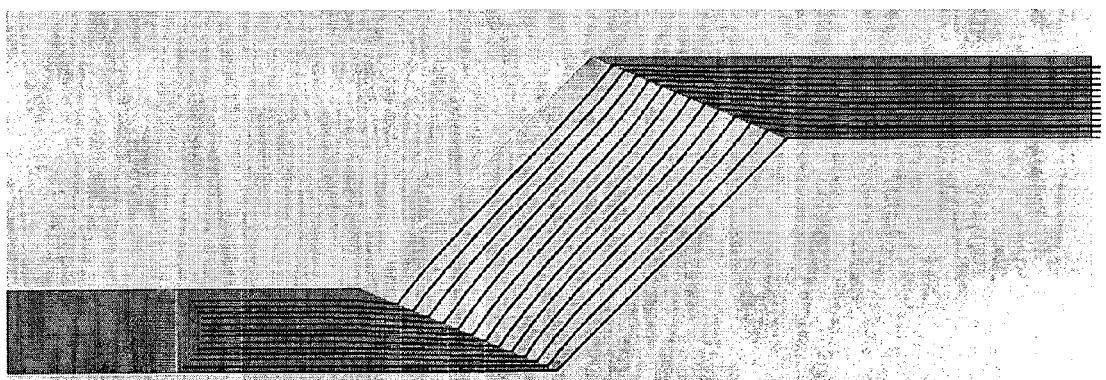

FIGS. 7A–C show numerical simulations of flow past two symmetrical interfaces, wherein black lines are used as "streaklines" to show simulated flow of material.

Figure 8A:
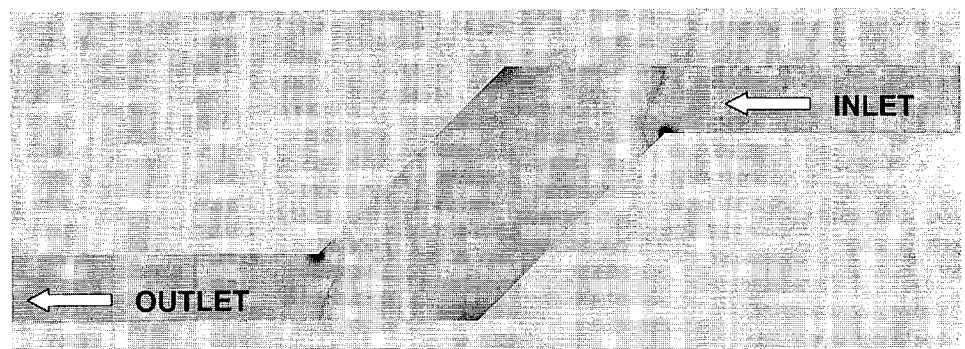
Figure 8B:
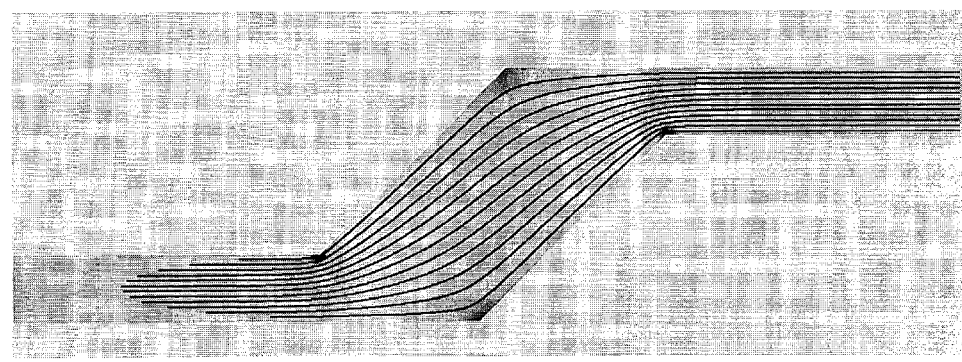

FIG. 8A and FIG. 8B show simulation images corresponding to an electrokinetic channel with the same wall geometry as that shown in FIG. 6 and FIG. 7.

Figure 9:
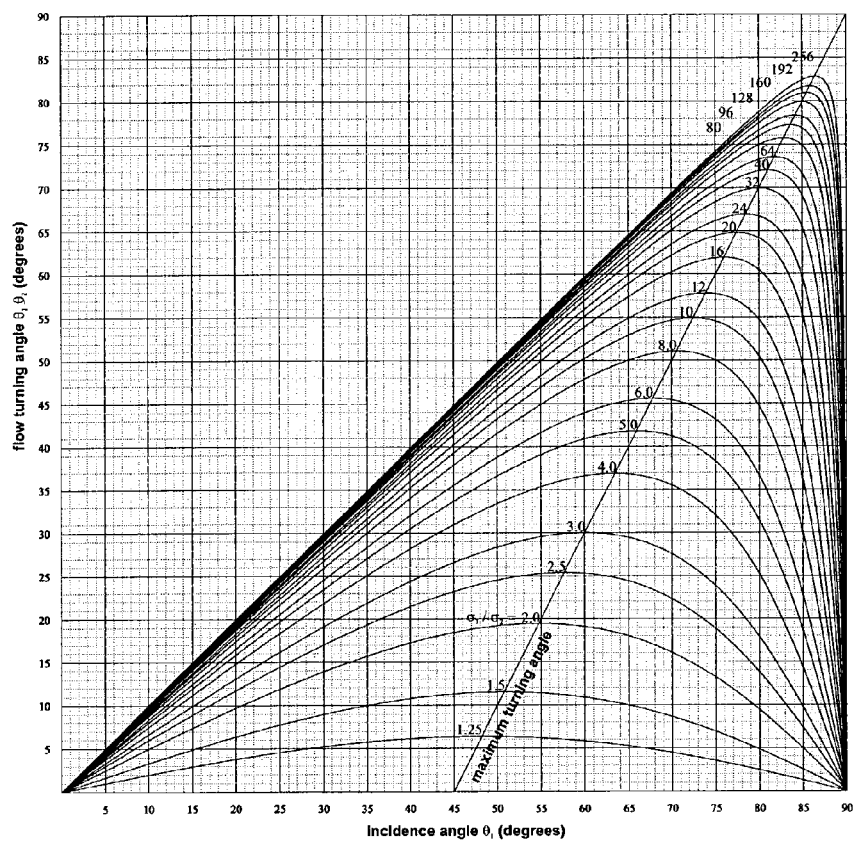

FIG. 9 shows the variation of the flow velocity turning angle, $\theta_1-\theta_2$ with the incidence-angle $\theta_1$ at selected interface permeability ratios.

Figure 10:
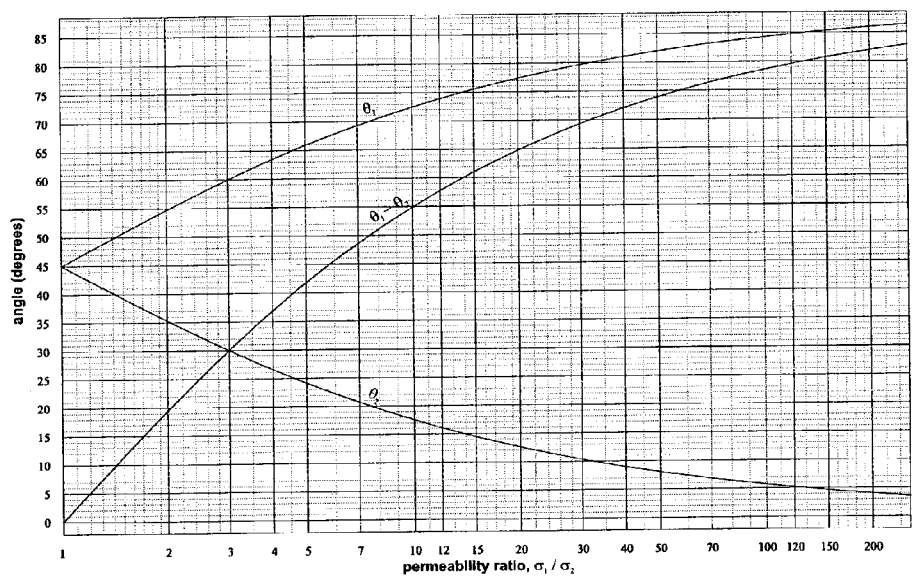

FIG. 10 shows the variation with interface permeability ratio of the incidence-angle, $\theta_1$, exit angle $\theta_2$, and flow velocity turning angle, $\theta_1-\theta_2$ at the maximum turning angle.

Figure 11A:
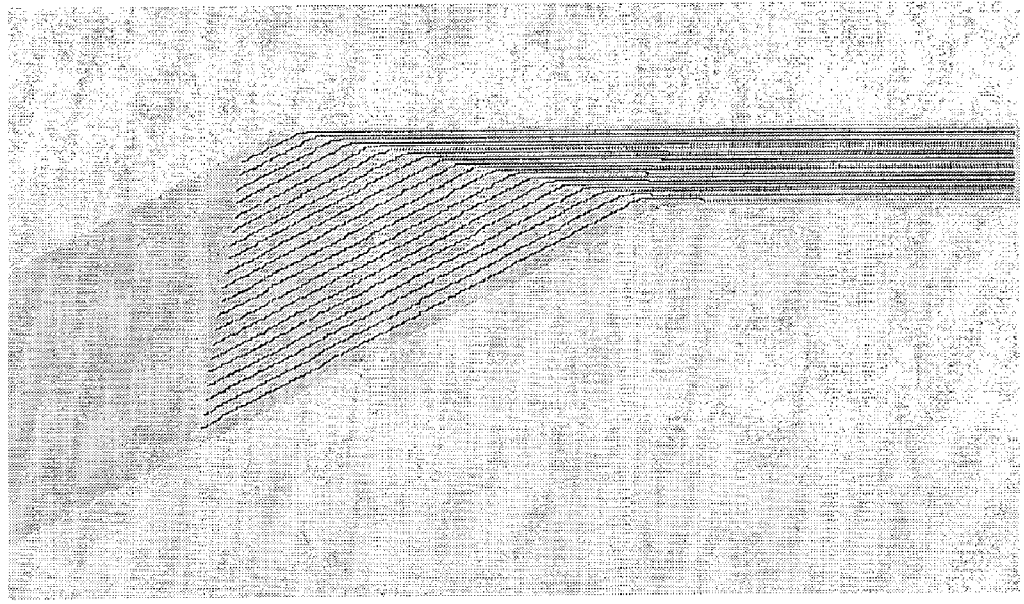
Figure 11B:
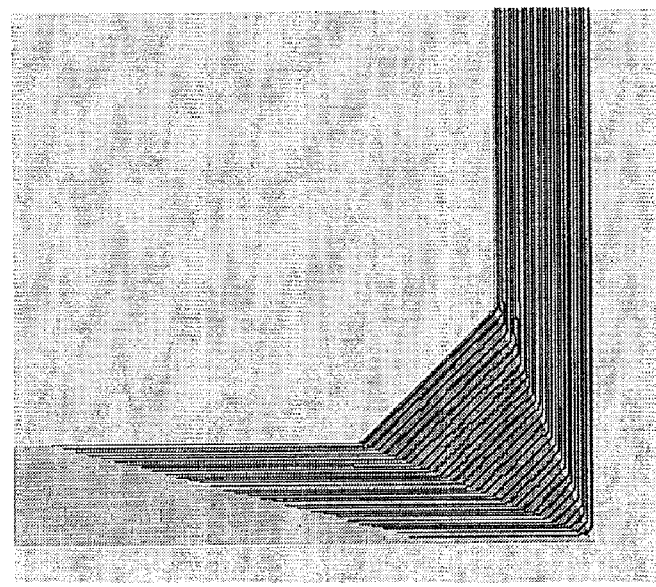
Figure 11C:
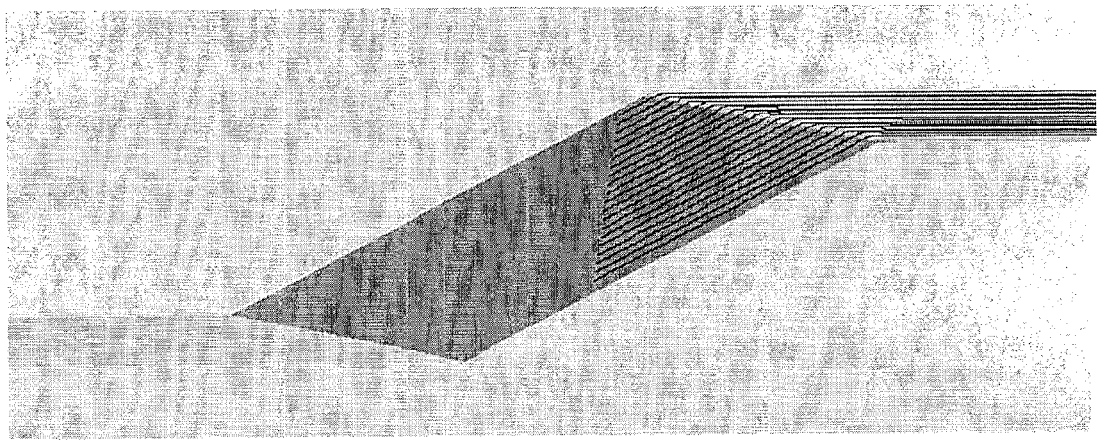

FIGS. 11A–C show a numerical simulation of flow streaklines and speed fields within devices based upon critical flow-turning angle 45° turns. FIG. 11A shows a design and simulation of the flow at an inclined interface designed to produce a 45° turn in the flow velocity angle at this maximum turning angle condition. FIG. 11B shows a numerical simulation of flow streaklines and speed fields within devices based upon critical flow-turning through two successive 45° turns, wherein the superimposed streaklines show pronounced skew in the 90° turn with respect to the flow direction. FIG. 11C shows a numerical simulation of flow streaklines and speed fields within devices based upon critical flow-turning through two offset 45° turns wherein the 45° offset nulls material skew at the second interface.

Figure 12A:
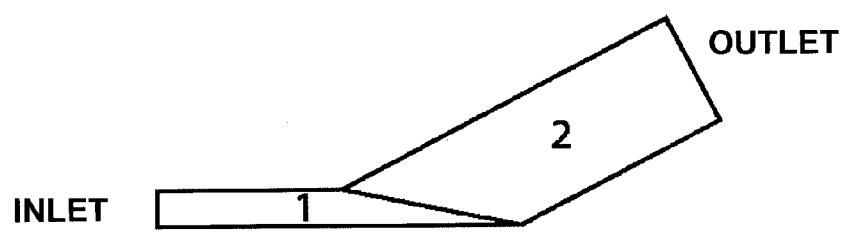

FIGS. 12A–E show subcritical turning interfaces and their use in channel expansions. The numbers 1 and 2 identify the high and low permeability regions, respectively. The interface in FIG. 12A is at the critical turning angle of 45°. The interfaces in FIG. 12B and FIG. 12C both subcritically turn the flow velocity by 10°. Rotation-free inline expansions, shown in FIG. 12D and FIG. 12E can be constructed by placing these interfaces back-to-back.

Figure 13:
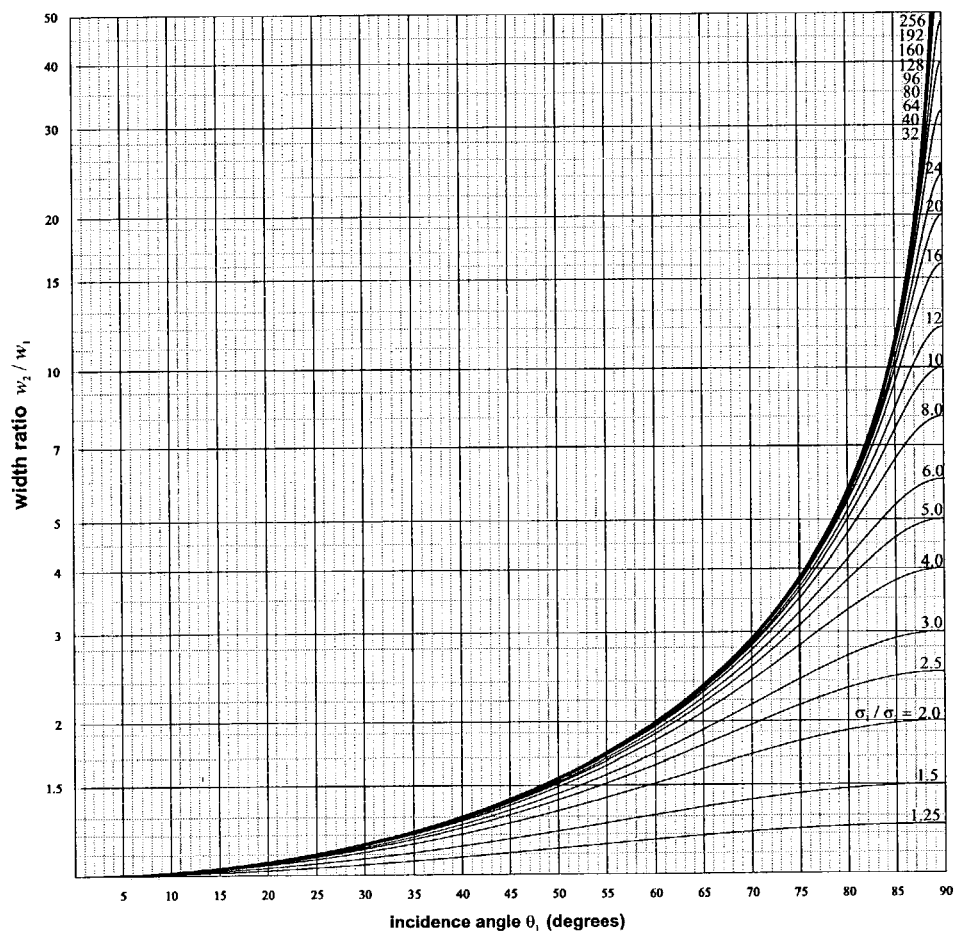

FIG. 13 shows the variation of the ratio of channel widths with incidence-angle across an interface having various permeability ratios: the high-incidence-angles produce much larger width changes than the low-incidence-angles. Channel expanders or reducers can be constructed by sequencing high incidence-angle and low incidence-angle interfaces.

Figure 14:
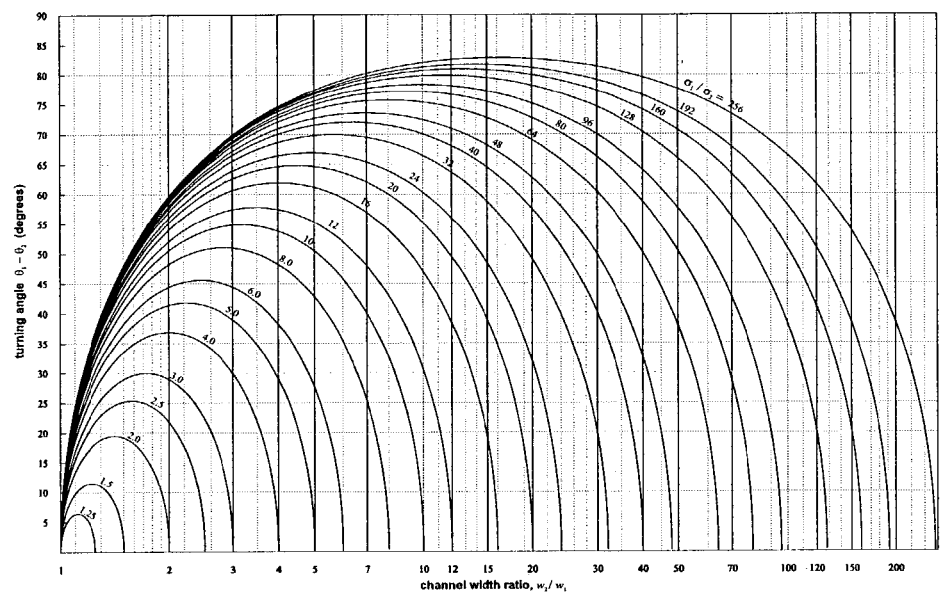

FIG. 14 shows the variation of the turning angle with channel-width ratio across an interface having various permeability ratios.

Figure 15:
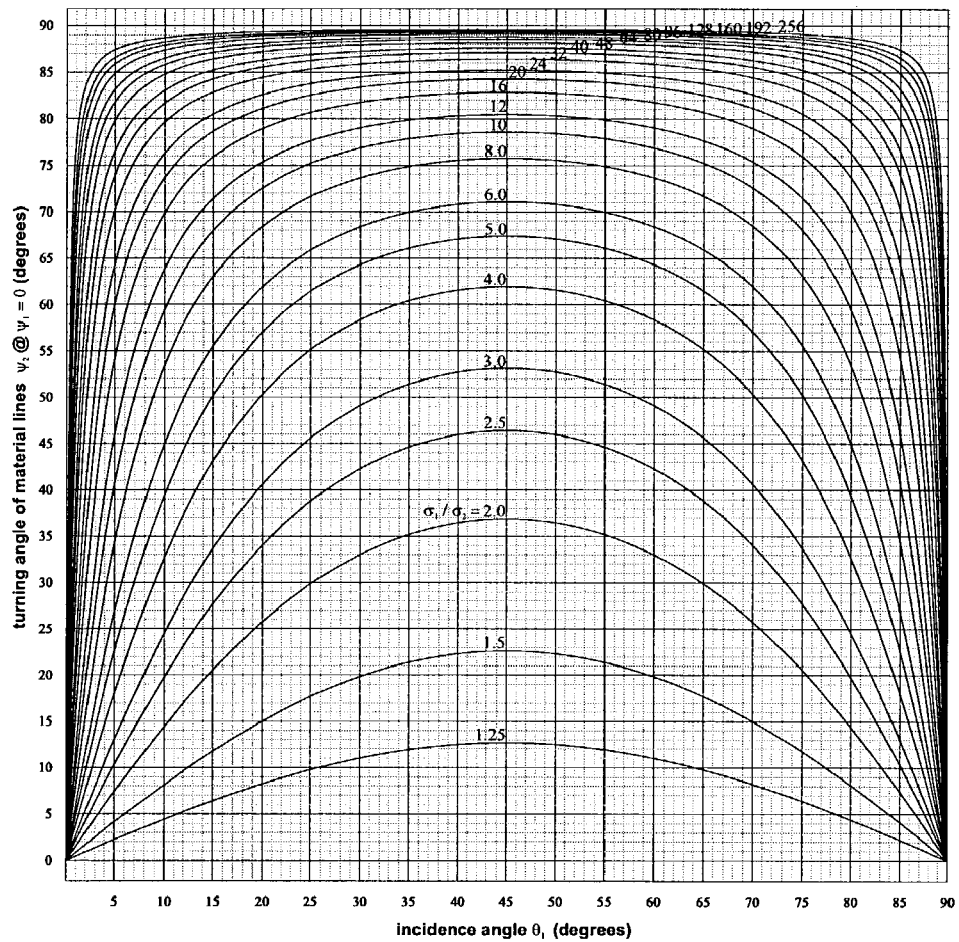

FIG. 15 illustrates the variation with incidence-angle and permeability ratio of the skew angle introduced by an interface to a material line that is initially perpendicular to the flow direction.

Figure 16:
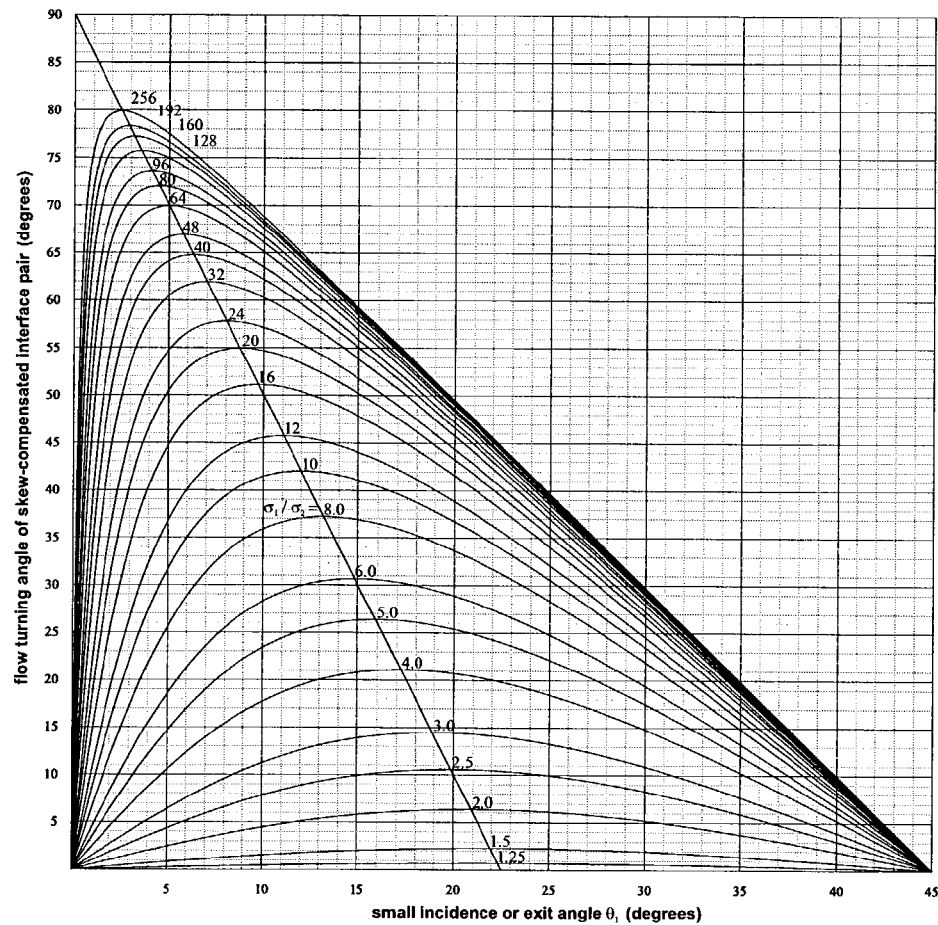

FIG. 16 shows the variation of the flow velocity turning angle of a skew-compensated interface pair with the smaller of the incidence or exit angles, $\theta_1$, at various permeability ratios.

Figure 17:
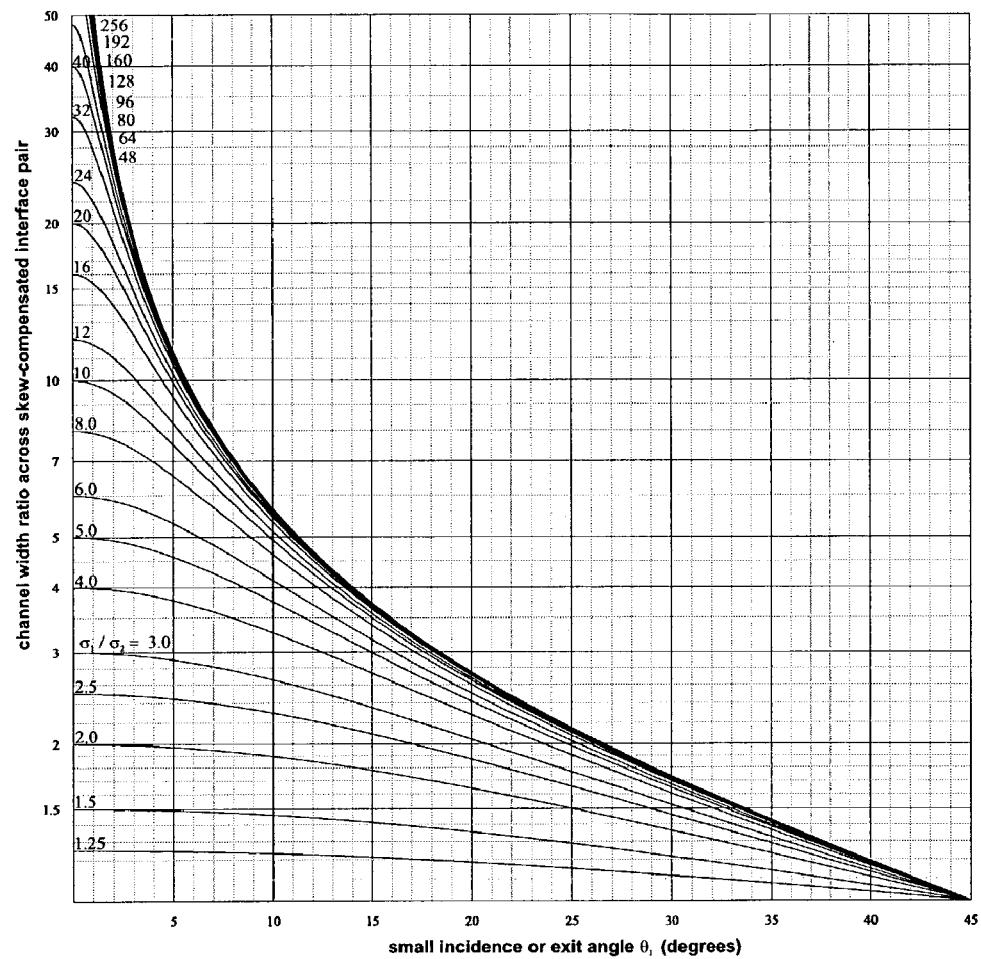

FIG. 17 shows the variation of the channel expansion ratio of a skew-compensated interface pair with the smaller of the incidence or exit angles, $\theta_1$, at various permeability ratios.

Figure 18A:
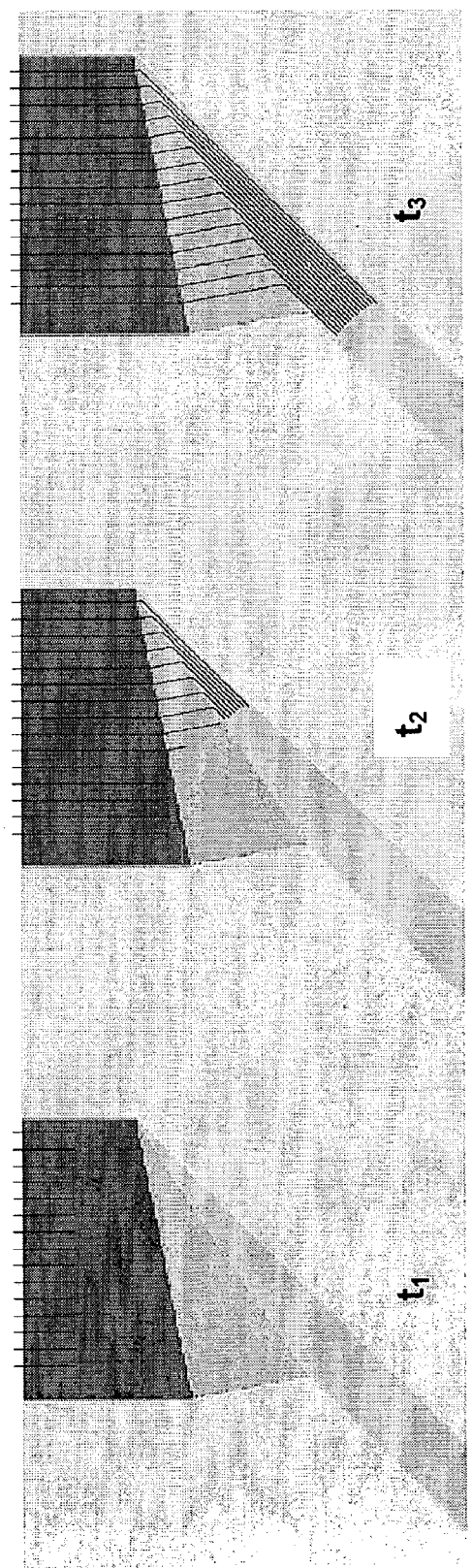
Figure 18C:
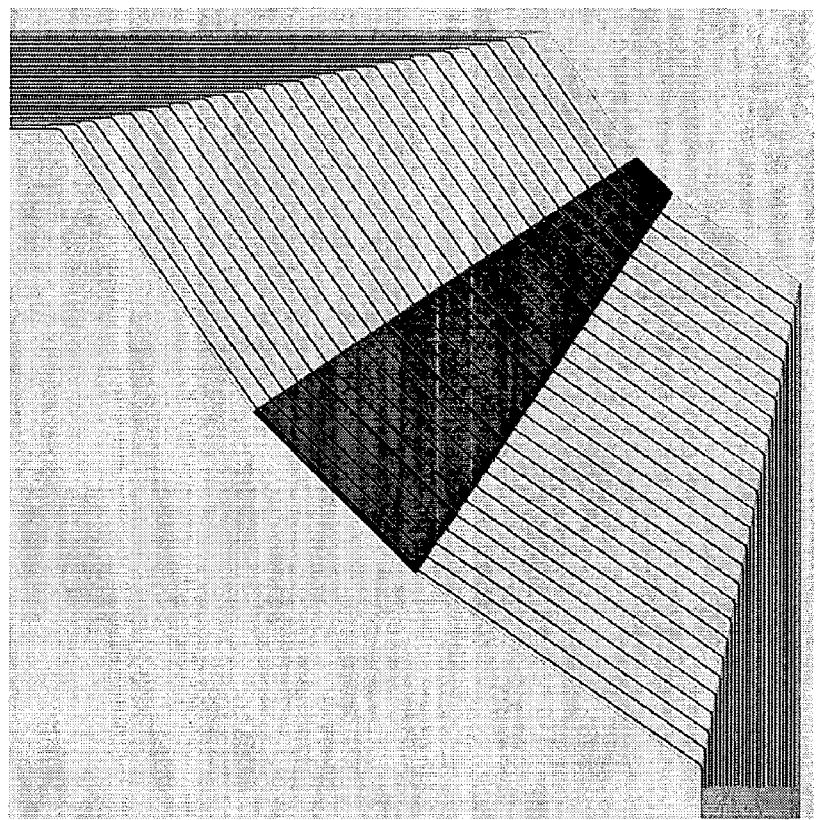
Figure 18B:
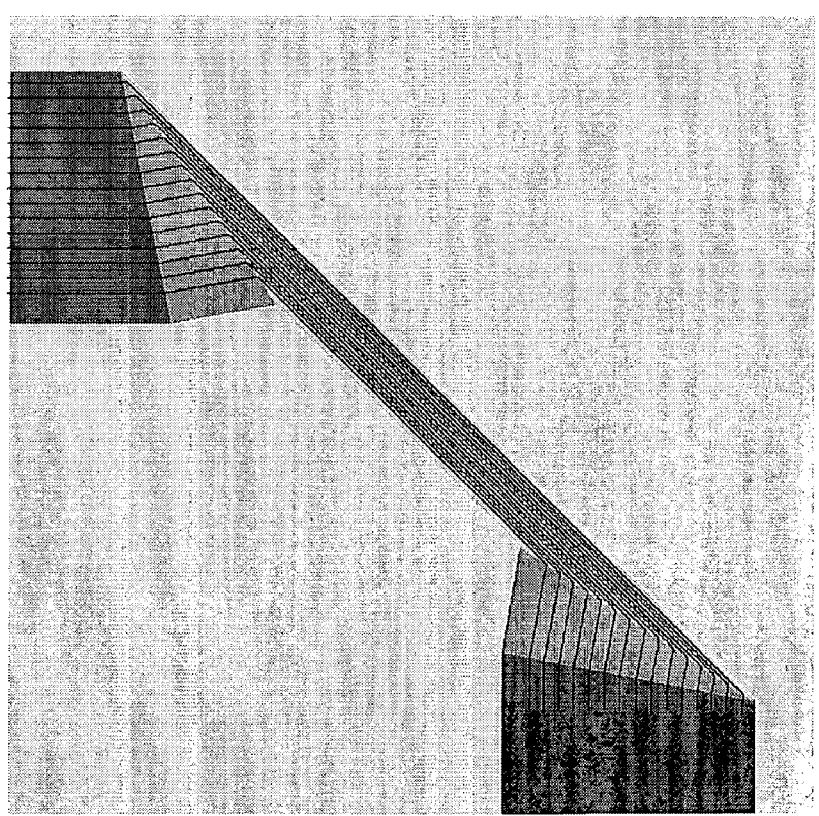

FIGS. 18A–C illustrate the flow simulation of a critical skew-compensated interface. FIG. 18A shows an interface that rotates the flow by 45° and narrows the channel by a factor of ~4.6. FIG. 18B shows the flow simulation of a non-expanding 90° turn designed by connecting the narrow channels of two prisms like that shown in FIG. 18A. FIG. 18C shows the flow simulation with an alternative turn that is constructed by connecting the wide channels of the prisms.

Figure 19B:
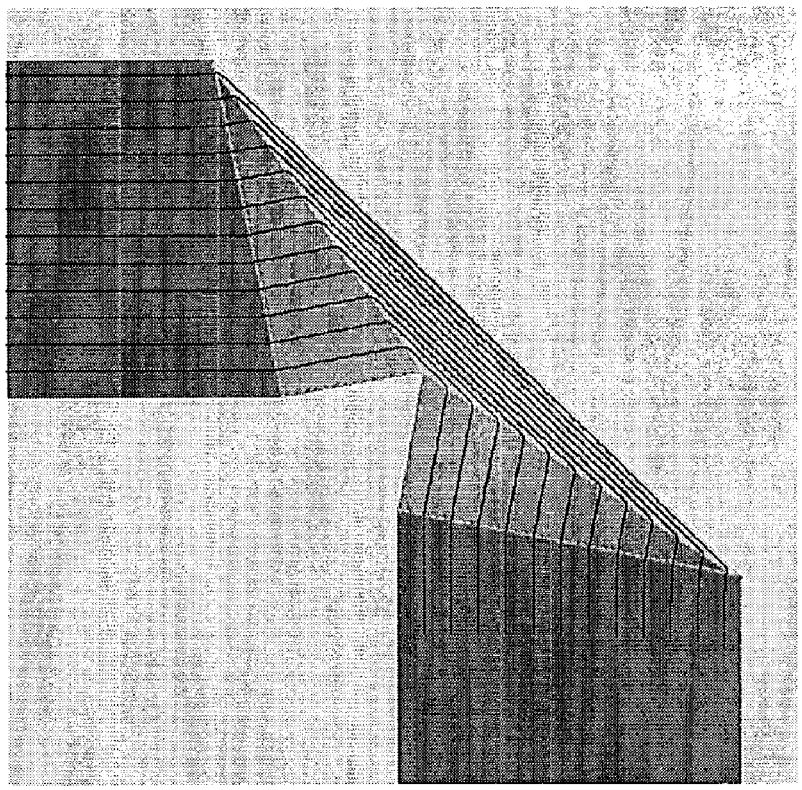
Figure 19A:
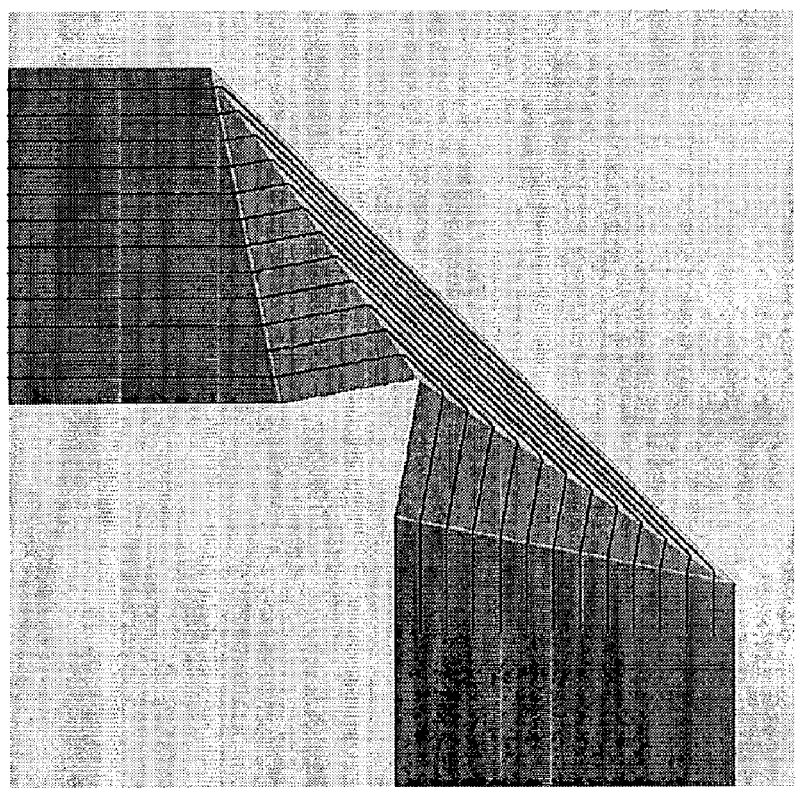
Figure 20A:
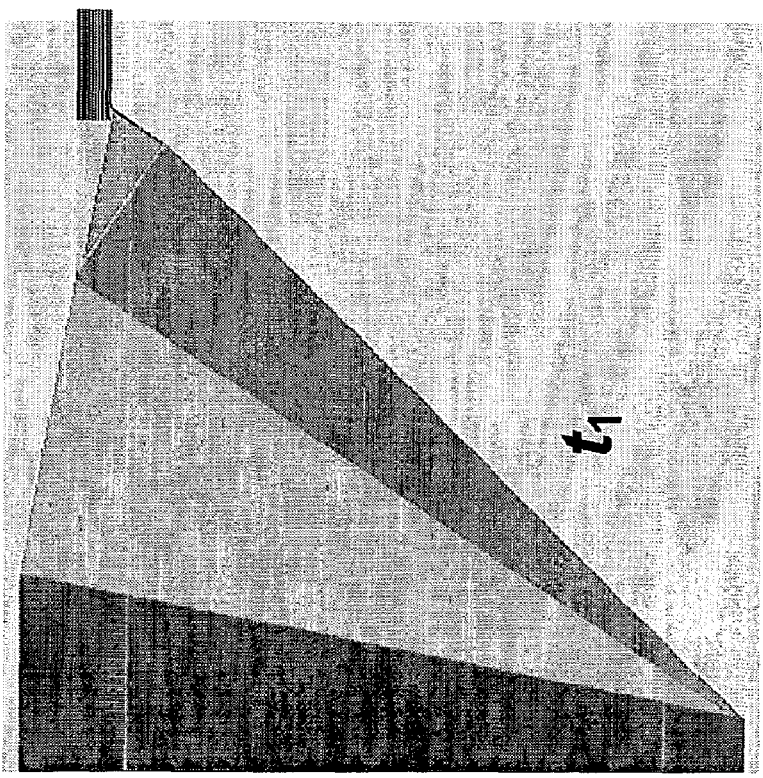
Figure 20B:
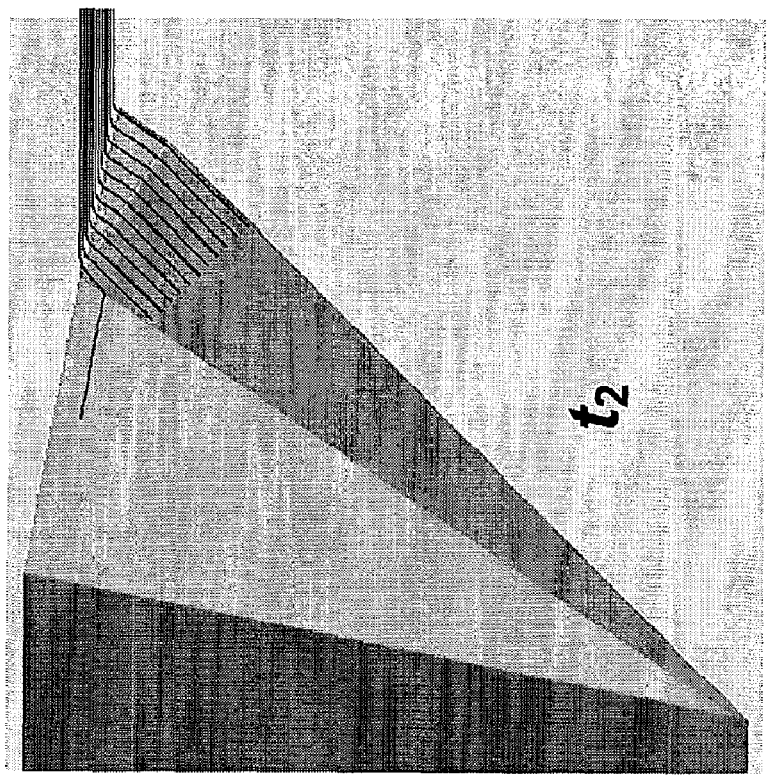
Figure 20D:
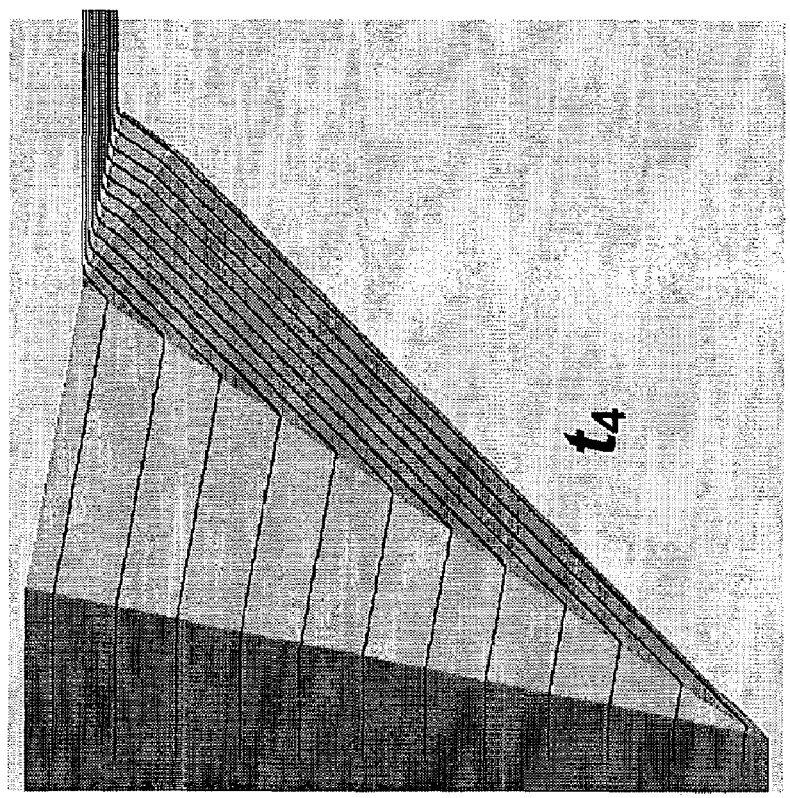
Figure 20C:
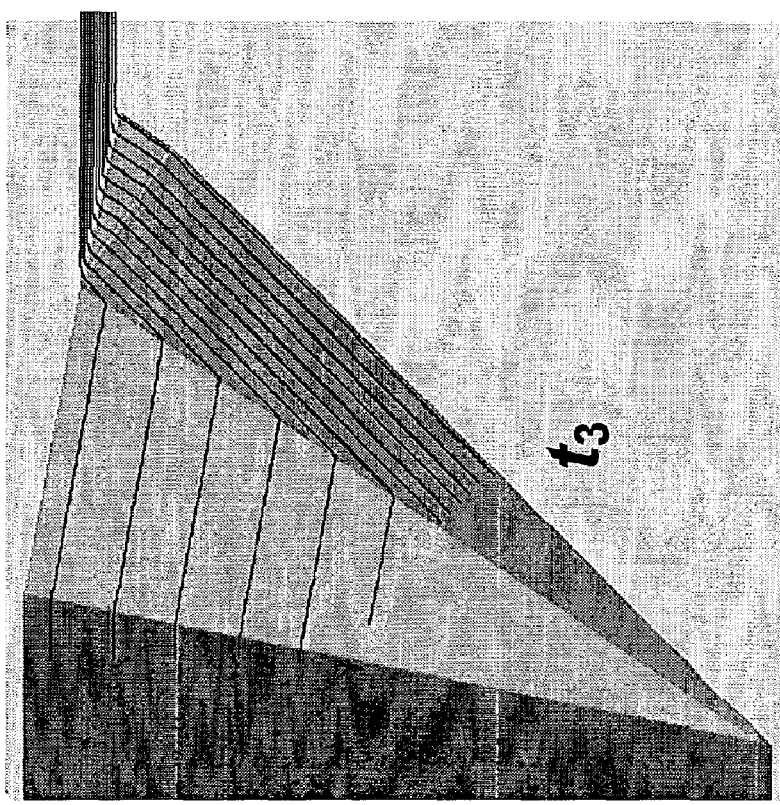
Figure 21B:
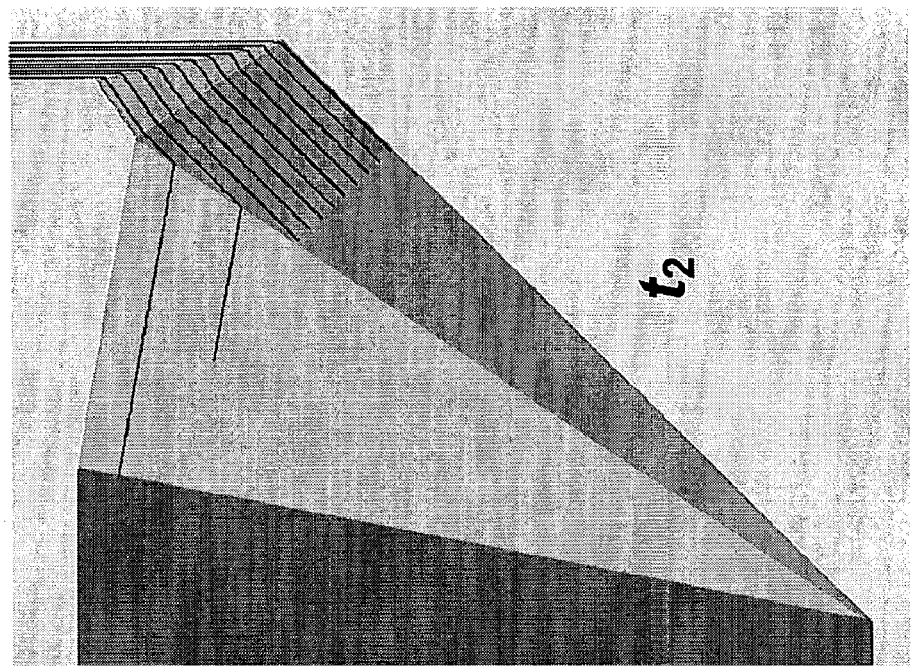
Figure 21A:
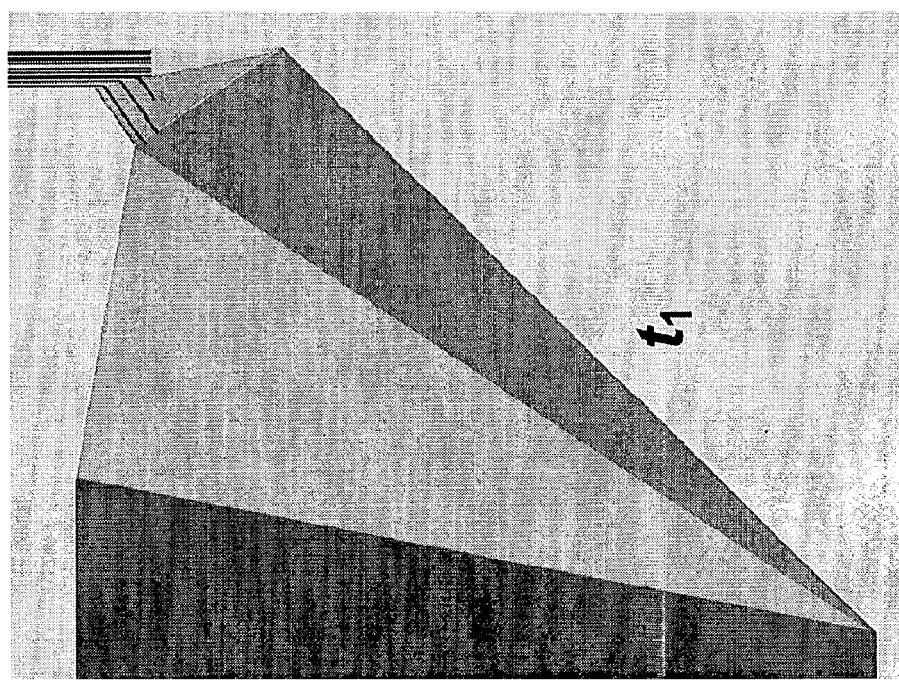
Figure 21D:
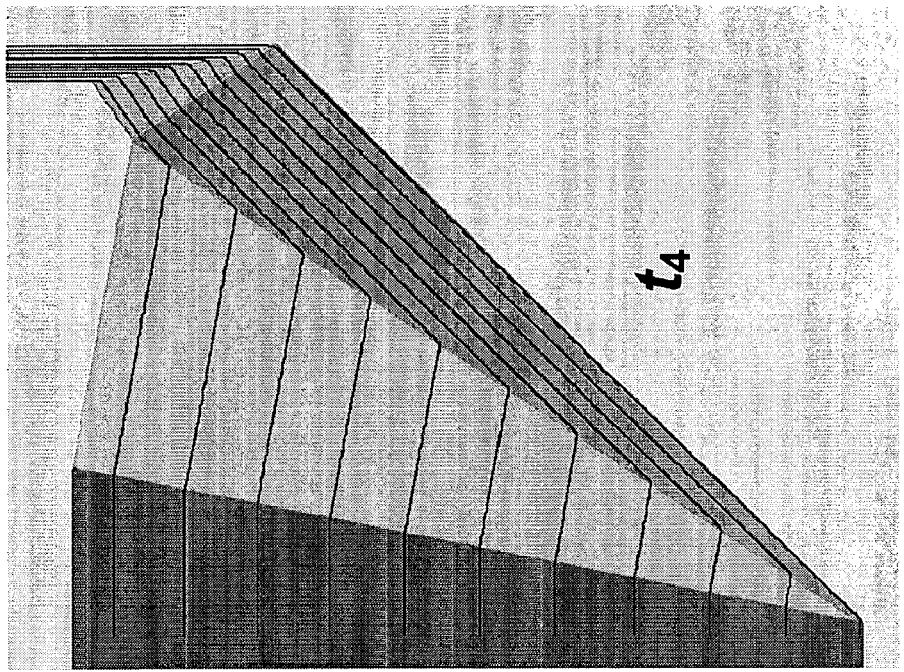
Figure 21C:
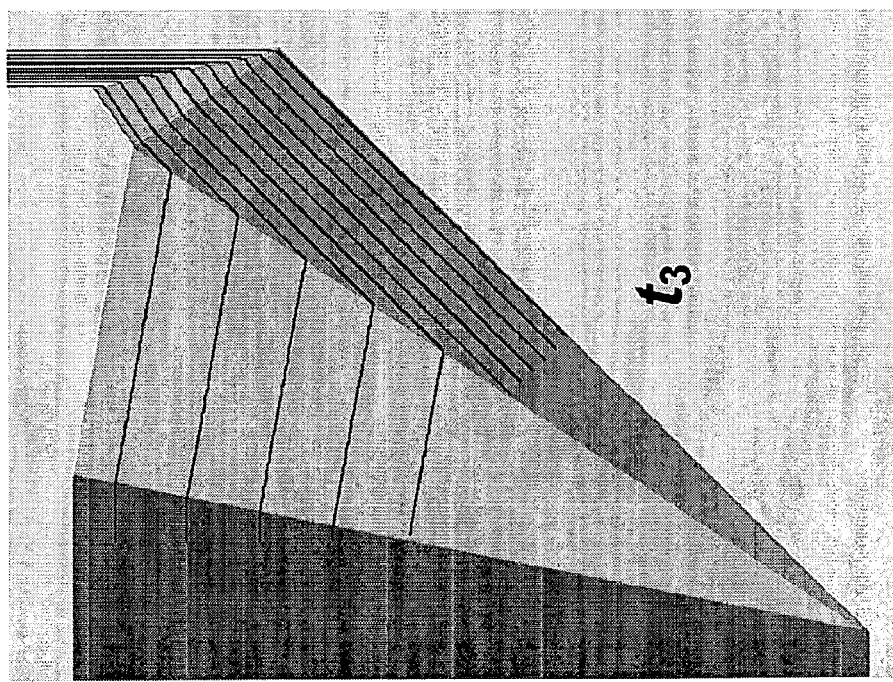

FIGS. 19A and 19B show the flow simulation of an on-design (left) and off-design (right) nonexpanding 90° turn. This design is the same as that is FIG. 18, but with the arbitrary length of the channel connecting the prisms shrunk to its minimum length.

FIG. 20 shows the flow simulation of an inline ~21-fold channel expander made from two prisms like that in FIG. 18A by connecting the wide port of one prism to the narrow port of the next.

FIG. 21 shows the flow simulation of a 90° ~21-fold channel expander made by connecting the wide port of one prism to the narrow port of the next in an alternative arrangement to that in FIG. 19.

Figure 5:
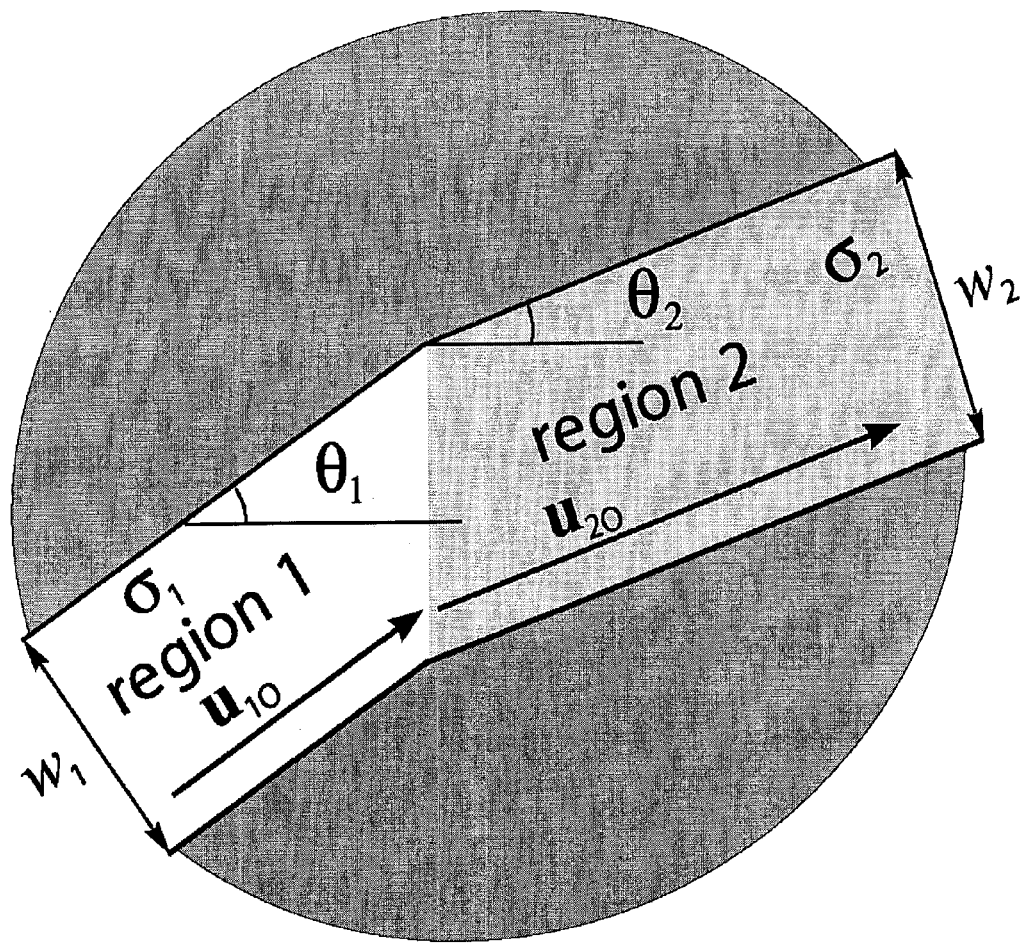
FIG. 5 shows a sketch of a conduction channel having a single interface between regions of two different permeabilities, $\sigma_1$ and $\sigma_2$.
Figure 22A:
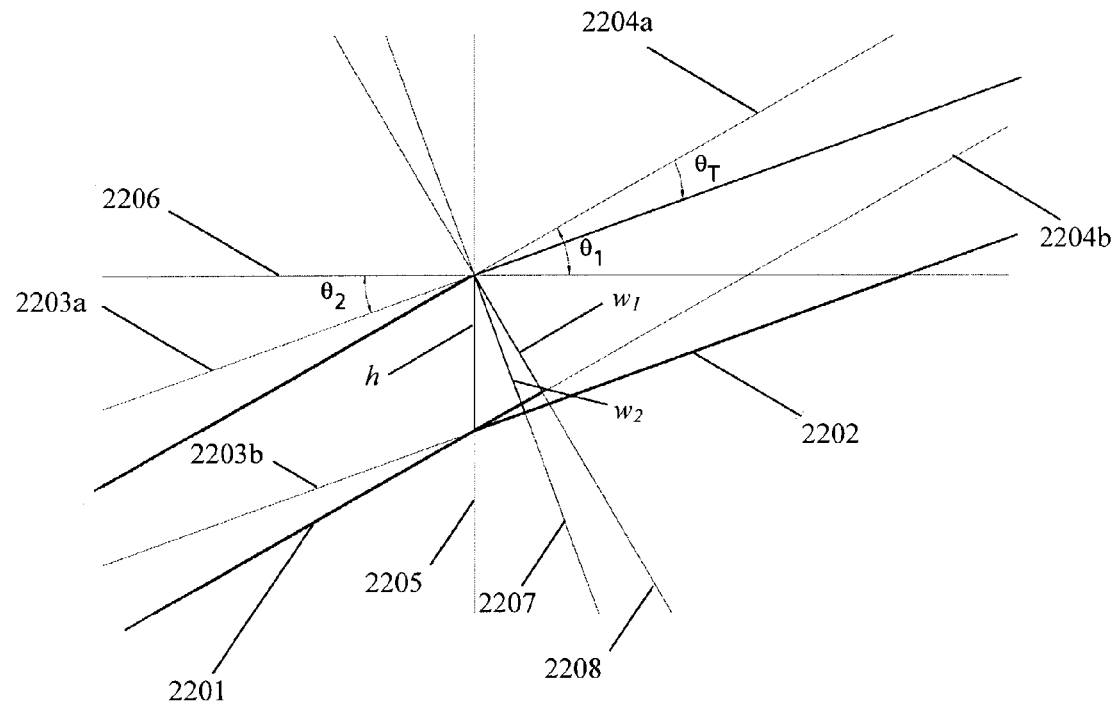
Figure 22B:
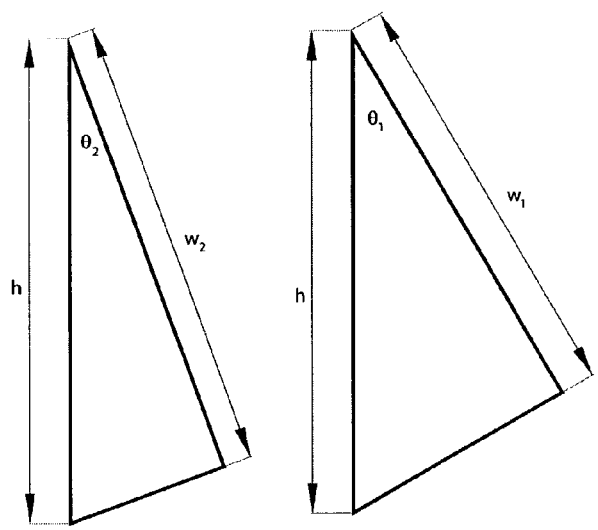

FIG. 22A and FIG. 22B shows a geometric diagram used to derive Eq. 7, where FIG. 22A represents the channels of FIG. 5, and where the right triangles shown in FIG. 22B correspond to the adjacent right triangles in FIG. 22A that share a common hypotenuse h (forming the interface between the two channel sections).

Figure 23A:
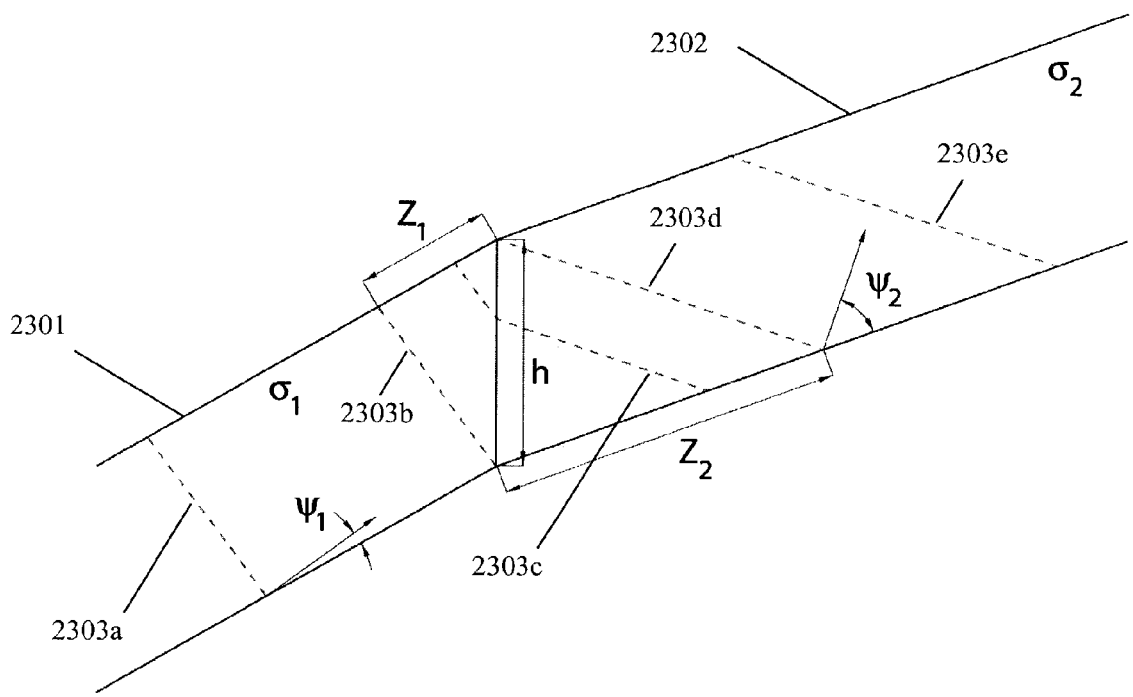
Figure 23B:
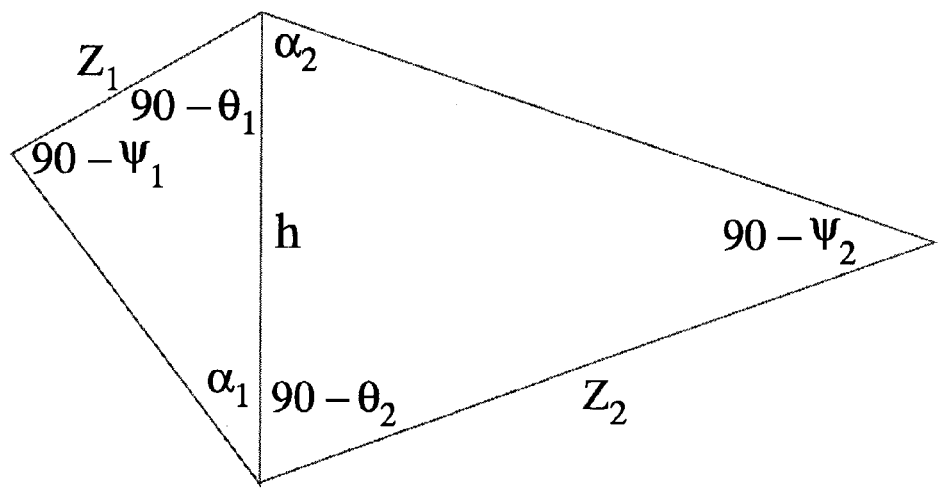

FIG. 23A and FIG. 23B show a second geometric representation of two intersecting flow channels used to derive Eq. 17, where FIG. 23A again represents the channels of FIG. 5 wherein material lines, shown as dashed lines, are skewed by an angle $\psi_1$, and where FIG. 23B shows right triangles sharing a common hypotenuse h (forming the interface between the channel) that are obtained from the geometric construction in FIG. 23A.

Figure 24A:
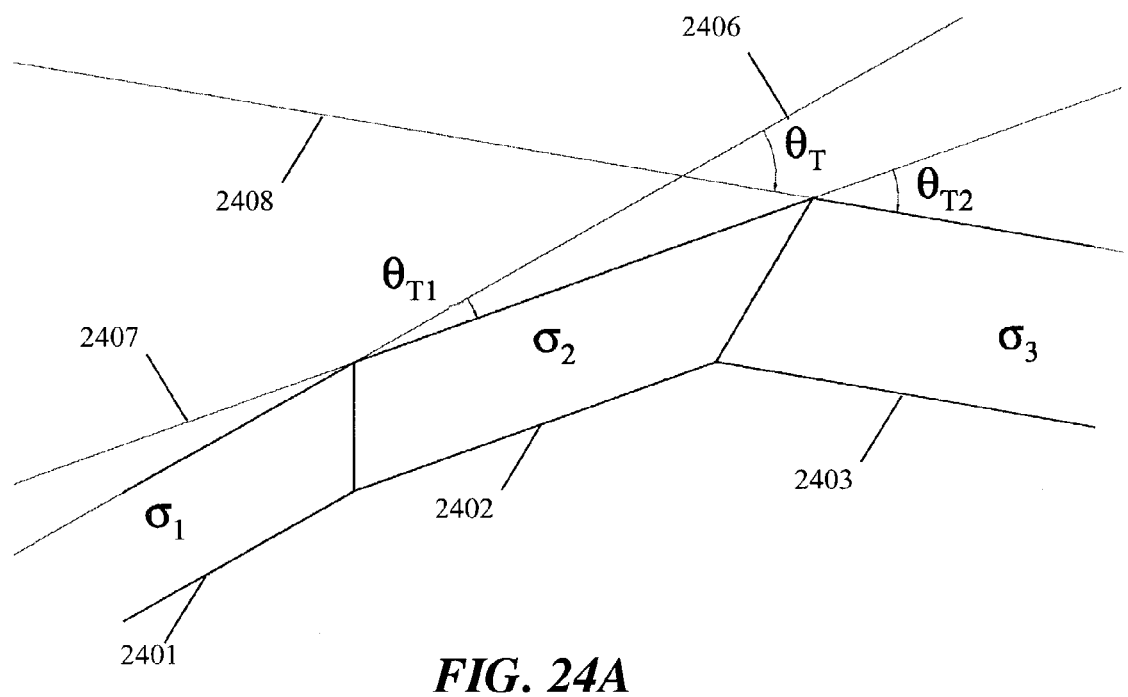
Figure 24B:
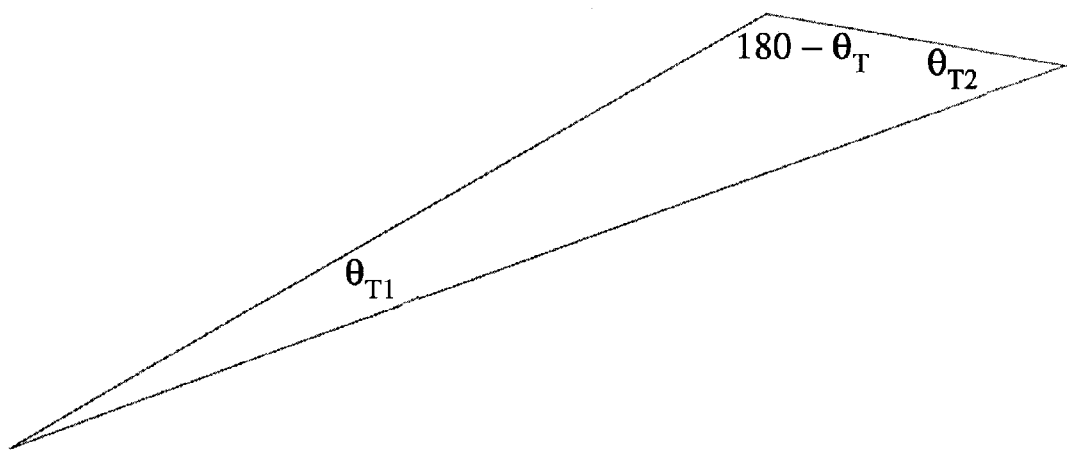

FIG. 24A and FIG. 24B show a third geometric diagram showing three intersecting channels used to derive Eq. 19, the skew-compensated turning angle, where FIG. 24A shows three intersecting flow channels where construction lines have been added parallel to the upper channel wall of each section to form the triangle shown in FIG. 24B.

Figure 25D:
Figure 25E:
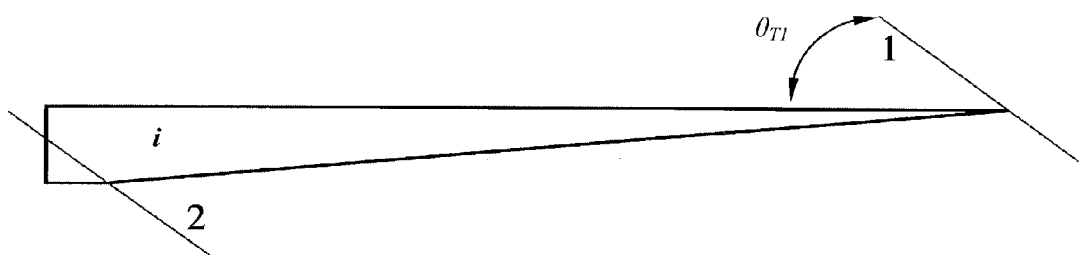
Figure 25F:
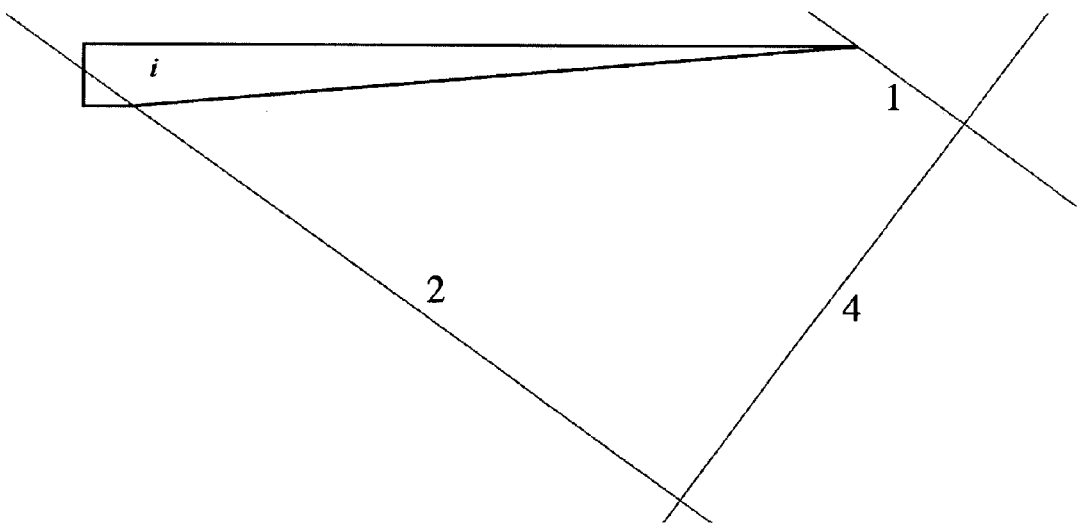
Figure 25G:
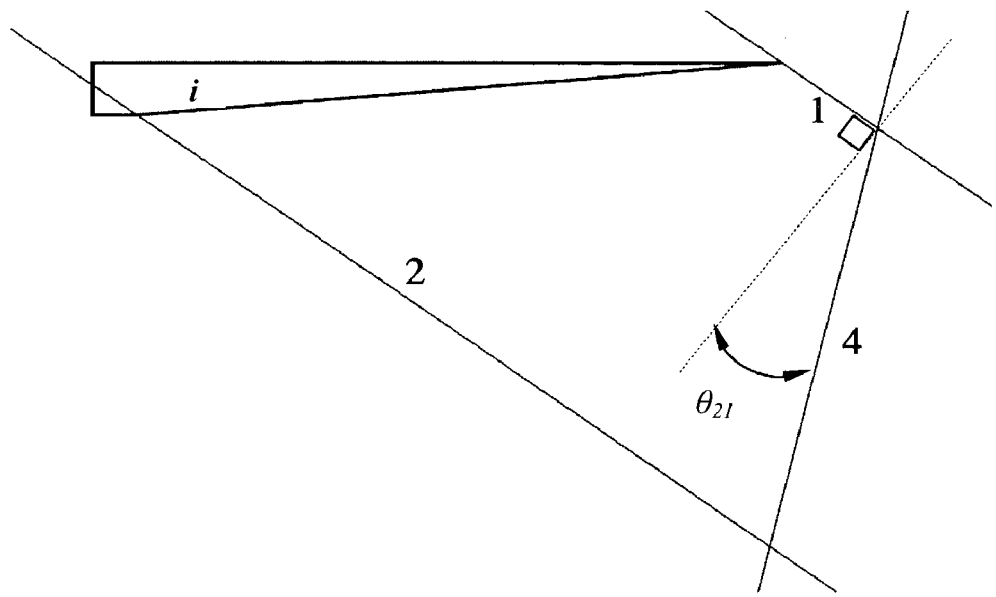
Figure 25H:
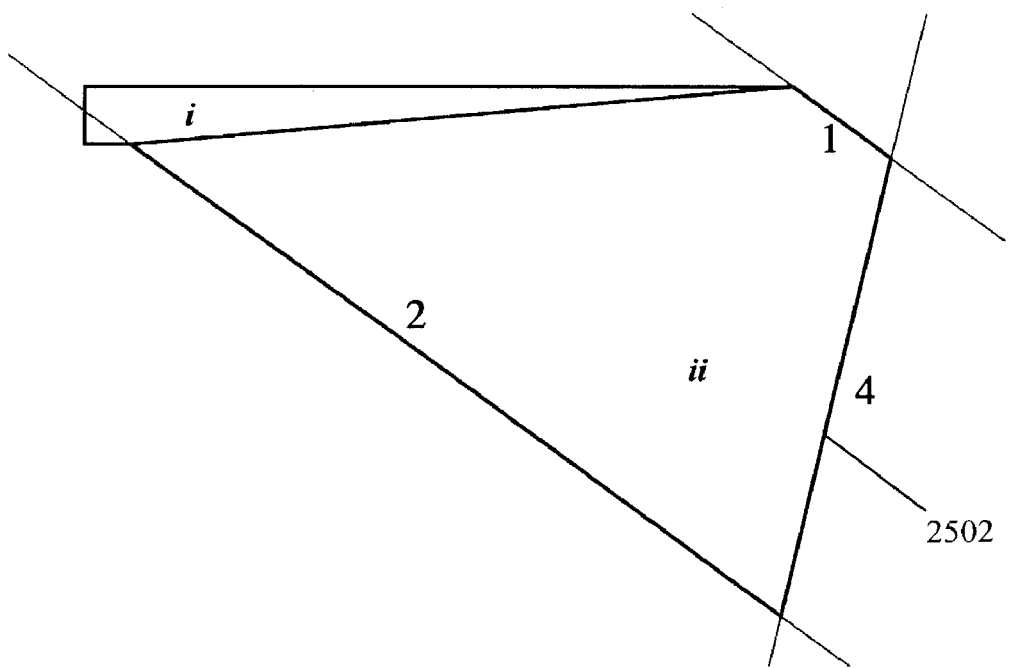
Figure 25I:
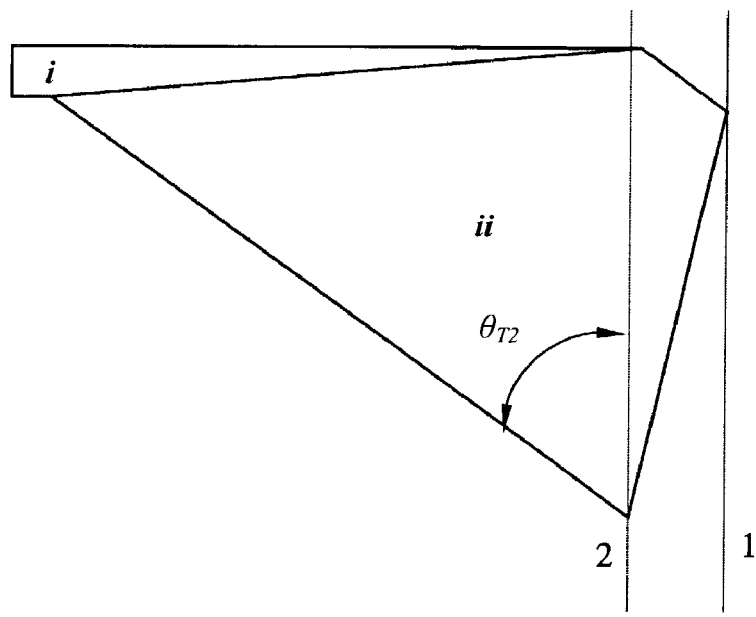
Figure 25J:
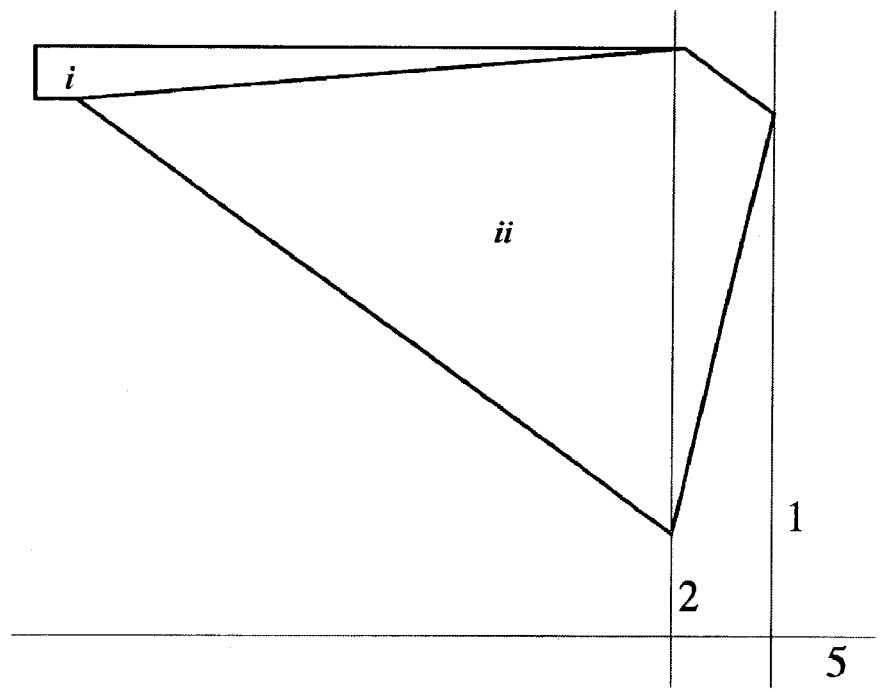
Figure 25K:
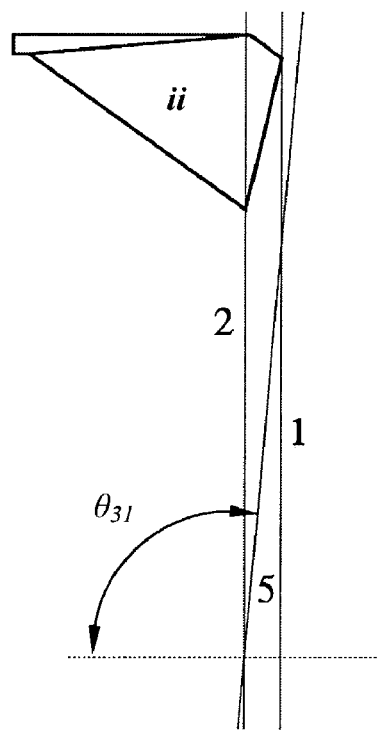
Figure 25L:
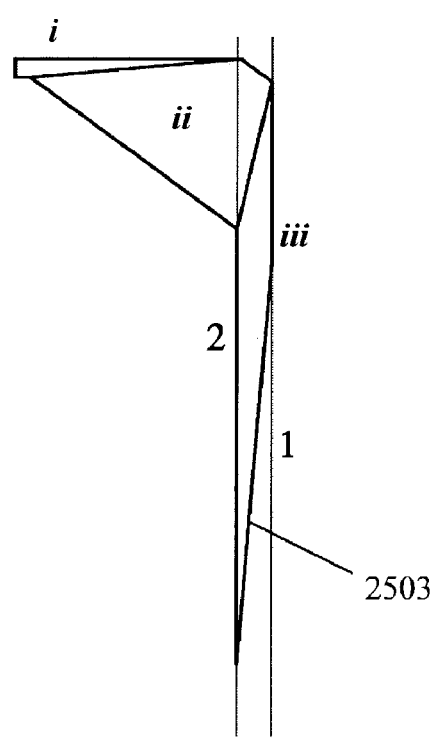
Figure 25M:
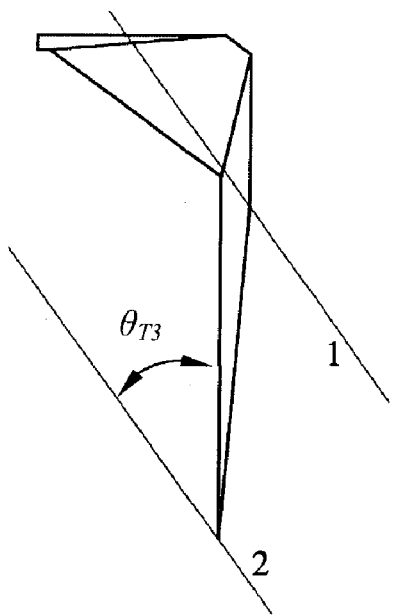
Figure 25N:
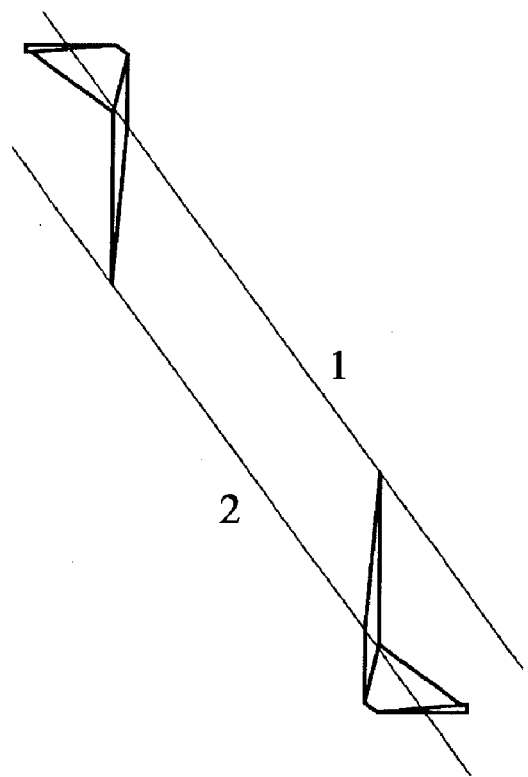
Figure 25O:
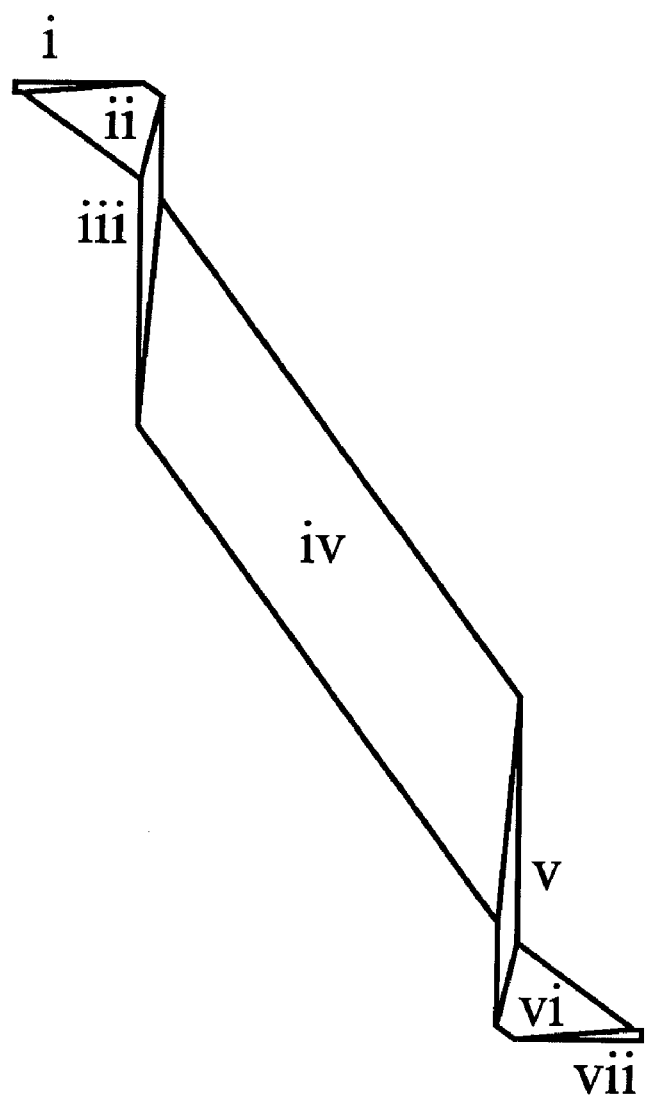

FIGS. 25A–O illustrate each of fifteen steps in the design of a skew-compensated expander using CAD software.

FIG. 26 shows the procedure used to change the length of various regions of FIG. 25.

FIGS. 27A–I show a three step process for designing a skew-compensated flow splitter using CAD software.

DETAILED DESCRIPTION OF THE INVENTION

The invention can be best understood by considering the mathematics of conduction, which appear in many physical contexts, and is among the simplest and most thoroughly studied of any physical process. A new general method for designing fluid conduction channels is outlined as below and the resulting channels can, in turn, be applied to provide channel segments which will function as turns, splitters, combiners, manifolds, and expanders for electrokinetic or pressure driven flows.

Consideration is given to the depth-averaged properties of the fluid flow in three-dimensional fluid systems. For this reason, variations in the third dimension (depth) do not appear explicitly in the following discussion. This consideration is appropriate for channels having the planar properties outlined the Summary of Invention above. For clarity, we define the mathematical details and apply semantics that are relevant to ideal electrokinesis. However, this semantic bias does not exclude the use of the methodology for other conduction-like transport. The velocity u of the conduction fluid is everywhere proportional to the driving force E:

$$u = \mu E, \quad (1)$$

where the coefficient $\mu$ is the mobility of the fluid. In this analysis the mobility and the fluid conductivity are constant everywhere. The fluid flux per unit width j is proportional to the conduction velocity by:

$$j = \sigma u, \quad (2)$$

where $\sigma$ is defined as the "conductance" or "permeability" of the conduction channel, which is permitted to vary across a straight interface in this analysis. While the terms "conductance" and "permeability" are intended herein to have the same meaning and may be used, therefore, interchangeably, this property will be referred to hereinafter as the "permeability" of the conduction channel. These semantics are correct physically for ideal electrokinesis and other forms of conduction in which the local flow velocity is independent of medium permeability.

Permeation is usually treated as a continuous subscale phenomenon whose constitutive coefficient is the permeability. Normally a large separation in length scales is needed to support this subscale notion because fluctuations from the randomness of the permeable medium must average to insignificance over the larger scales. In contrast, the separation in length scales required to attach a meaningful permeability to an orderly medium such as a uniform patterned array is surprisingly small: roughly an order of magnitude.

Figure 1A:
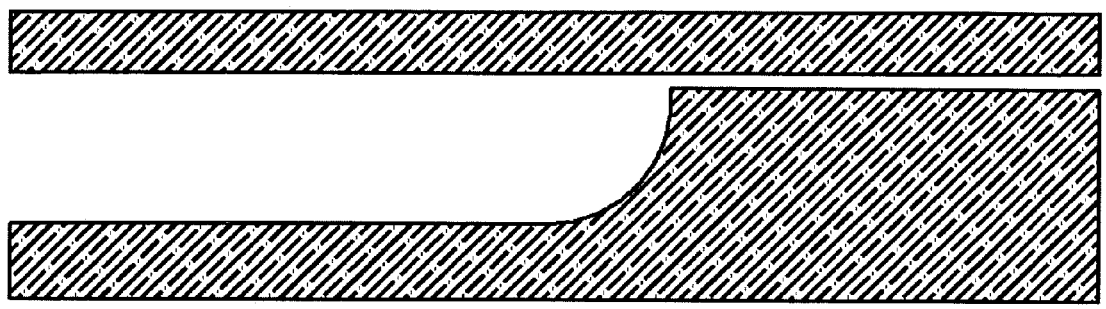
Figure 1B:
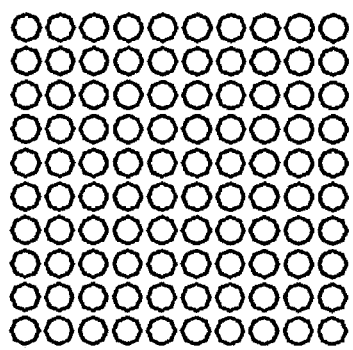
Figure 1C:
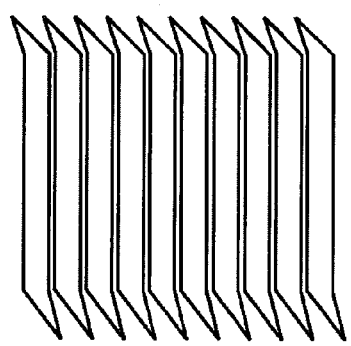
Figure 1D:
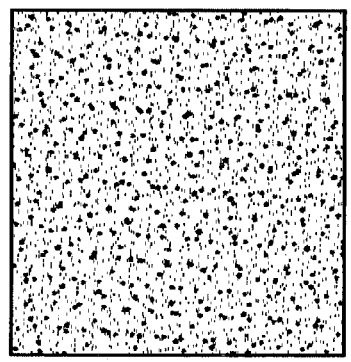

FIG. 1A–FIG. 1D shows several examples of subscale designs that modify the permeability of a channel. In a quasi-planar microsystem, the permeability of a channel, as defined in Eq. 2, is proportional to the channel depth. A two or more level etched microsystem, for example, can be used to implement these designs as in FIG. 1A. Alternatively, the effective permeability of a channel can be lowered with respect to an open channel by blocking part of the channel; for example by filing the channel with array of posts (FIG. 1B) or channel-aligned parallel columns (FIG. 1C). Another technique is to fill the channel with a porous media, such as with various particles of various insulating materials such as high dielectric micro- or nanoparticulate materials; packed beads such as polymer, glass, silica, or ceramic, or of any other insulating material; glass, ceramic, or other porous insulating frits; porous monolithic media such as porous polymers, porous sol-gels; and glass wool or polymer yarns, or the like, and combination thereof (FIG. 1D). These methods generate varying amounts of hydrodynamic dispersion at the interface and throughout the conduction channel and can be used separately or in combination.

Figure 2:
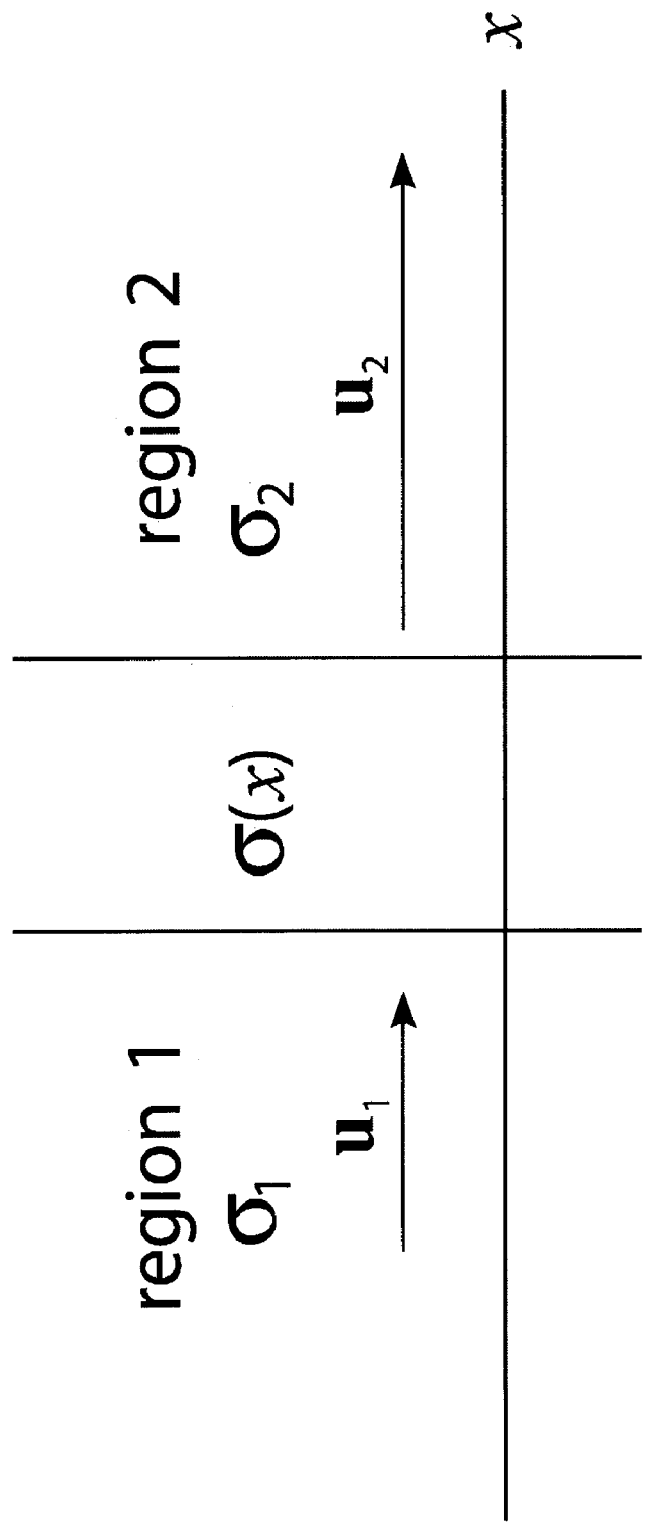

To analyze steady fluid conduction past a permeability change, we consider first the infinite one-dimensional conduction channel sketched in FIG. 2, having a uniform permeability $\sigma = \sigma_1$, in region 1, left of a finite transition region, and a uniform permeability $\sigma = \sigma_2$ in region 2, right of a transition region. Inside the transition region, the permeability variation is unspecified but bounded so that $0 < \sigma < \infty$ everywhere in the conduction channel.

Continuity requires a constant fluid flux per unit width j throughout the channel, such that:

$$j_1 = j_2 \rightarrow \sigma_1 u_1 = \sigma_2 u_2, \quad (3a)$$

or $$\sigma_1 \mu E_1 = \sigma_2 \mu E_2. \quad (3b)$$

This simple one-dimensional consequence of continuity will be used in the next section to establish a compatibility relation for low-dispersion, quasi-two dimensional flow-channel design.

A Special Case of Two-Dimensional Conduction Across a Permeability Change

Figure 3:
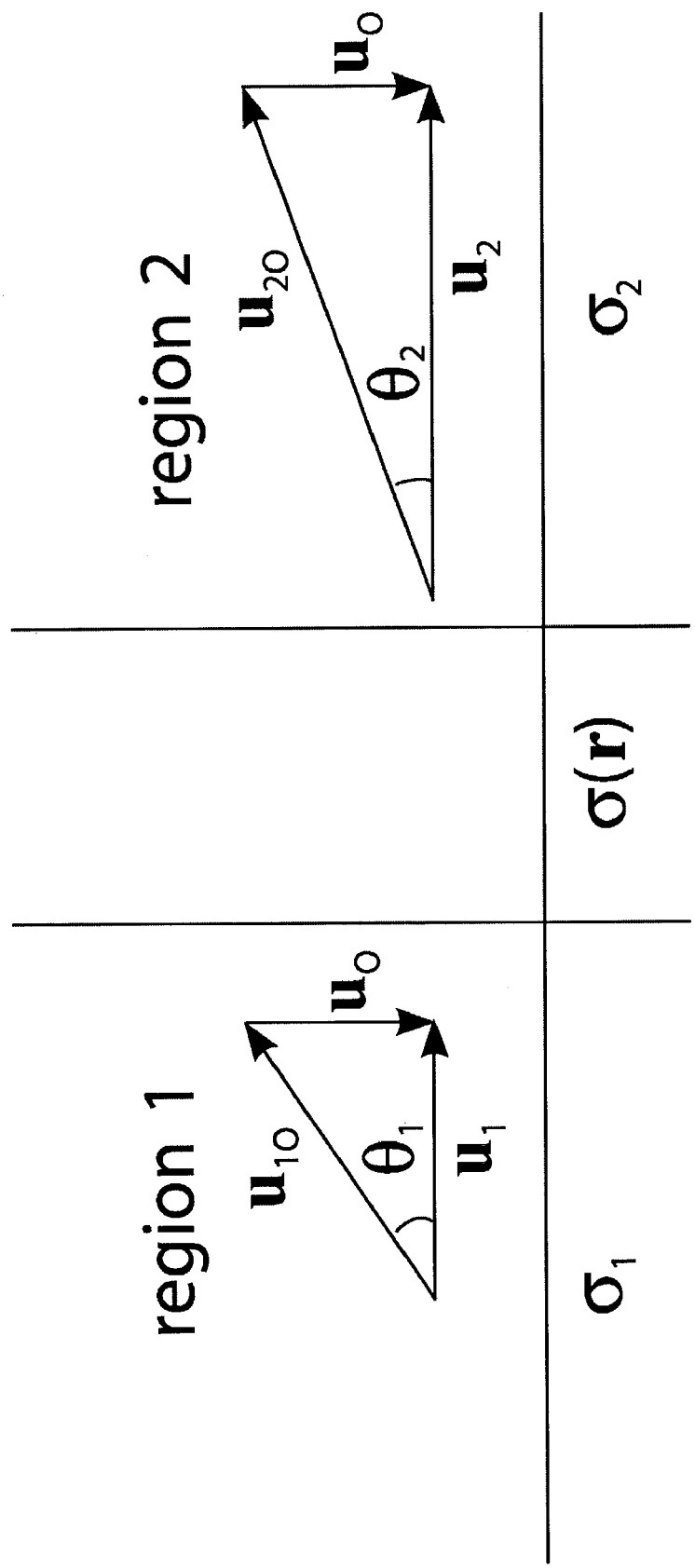

FIG. 3 shows the system in FIG. 2 from the standpoint of an observer moving at a steady velocity $u_o$ along the interface, i.e., $u_o \cdot \nabla \sigma = 0$. Because the position of the interface is steady in this moving frame, Eq. 1 still holds and by extension:

$$\sigma_1 u_{1o} \cdot \hat{n} = \sigma_2 u_{2o} \cdot \hat{n}, \quad (4)$$

and $$u_o = u_{1o} - u_{1o} \cdot \hat{n} = u_{2o} - u_{2o} \cdot \hat{n}, \quad (5)$$

where $\hat{n}$ is a unit vector normal to the interface, i.e., $$\hat{n} \equiv \frac{\nabla \sigma}{\|\nabla \sigma\|} \quad (6)$$

everywhere $\nabla \sigma$ is finite.

In variables that are more suitable for design, these simultaneous equations can be rearranged to yield:

$$\frac{\tan \theta_1}{\sigma_1} = \frac{\tan \theta_2}{\sigma_2}, \quad (7)$$

and $$u_{1o} \sin \theta_1 = u_{2o} \sin \theta_2 \quad (8)$$

where $u \equiv \|u\|$ and $\theta_1$ and $\theta_2$ are the flow angles shown in FIG. 3. Eq. 7 resembles Snell's law of refraction, except tangents of the propagation angles are matched instead of sines. Eq. 8 describes how the speed varies across the interface.

Eqs. 7 or 8 can be considered "compatibility" conditions for locally one-dimensional flow in regions 1 and 2. In other words, if a conduction channel interface is designed to satisfy Eq. 7, the flow everywhere in region 1 will have a uniform velocity $u_{1o}$ region 2 will have a uniform flow velocity $u_{2o}$.

In order to describe the motion of flow through a conduction channel of interest it is often useful to visualize the motion of so-called "material lines" through the channel. Material lines are understood by those with skill in these arts to mean a locus of points propagating from initially linear sets of points representing the fluid, as these points track the distortions the fluid undergoes as it propagates through a flow channel. For the present purpose these lines are visualized in two-dimensions as the set of parallel linear lines shown as elements 2303a through 2303e in FIG. 23A.

Figure 4:
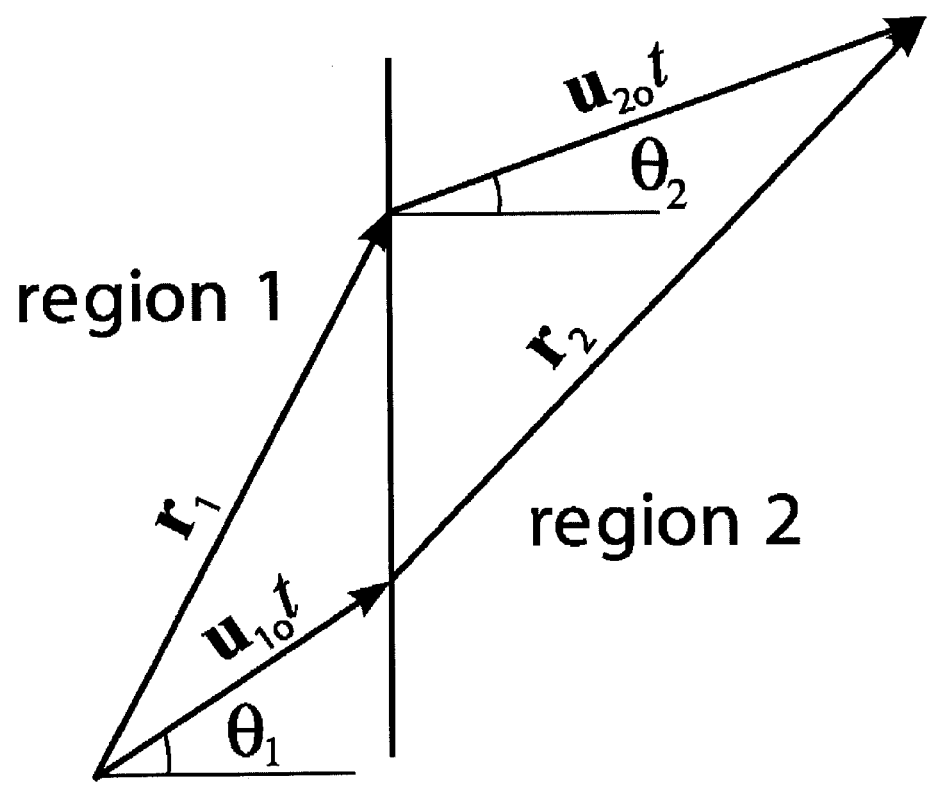
FIG. 4 illustrates a diagram of a material line represented by $r_1$ being distorted as it passes through the interface into the material line represented by $r_2$. A tilted interface satisfying the compatibility relation can rotate and stretch but not curve material lines.

In the case of flows satisfying the compatibility condition of Eqs. 7 or 8, the only place where the material lines are distorted or rotated is at the interface. FIG. 4 shows an idealization of the system in which the interface is abrupt compared to the length of the initial material line (represented by the vector $r_1$). This vector is drawn in FIG. 4 as one end reaches the interface. The other end reaches the interface after a time t having propagated through the vector $u_{1o}t$. During this period, the other end propagates through region 2 by the vector $u_{2o}t$, consequently:

$$r_1 - u_{1o}t = r_2 - u_{2o}t, \quad (9)$$

but, $$t = \frac{r_1 \cdot u_{1o}}{u_{1o} \cdot u_{1o}} \quad (10)$$

$$r_2 = r_1 + (u_{2o} - u_{1o})\frac{r_1 \cdot u_{1o}}{u_{1o} \cdot u_{1o}}. \quad (11)$$

so

Eq. 2 is an explicit equation for the distorted material line represented by $r_2$ in terms of the undistorted material line, $r_1$, and the velocities on both sides of the interface, $u_{1o}$ and $u_{2o}$. The simplest implementation of such a design is a flow channel having a single internal interface whose side-walls are oriented according to Eq. 7, as shown in FIG. 5. The widths $w_1$ and $w_2$ of the conduction channels in regions 1 and 2 in FIG. 5 obey the relation:

$$\frac{w_1}{\cos\theta_1} = \frac{w_2}{\cos\theta_2}. \quad (12)$$

The inclined interface between channels having dissimilar permeabilities can be viewed as a device primitive that:
  Rotates the conduction flow;
  Changes the conduction velocity/time-of-flight;
  Widens the conduction channel; and
  Rotates and deforms material lines of the flow.

So far, issues of the entry and exit boundary conditions have been avoided by assuming an infinite domain. The domain can be truncated provided the entry- and exit-flow conditions are compatible with the uniform flow in the respective regions, i.e., $$u_i = u_{io}, \quad (13a)$$

and $$\nabla u_i = 0, \quad (13b)$$

on the entrance to region i=1 or 2. To illustrate the effect the compatibility condition of Eq. 2, FIGS. 7A–C show numerical simulations of the speed field and flow streaklines within three instances of a system of two interfaces. The gray-scale map depicts the speed field: white and black are respectively the highest and lowest speeds. In FIG. 7A, compatibility is not satisfied for either interface because the permeability ratio $\sigma_1/\sigma_2$ is half that required by Eq. 2. Consequently, the speed field is not uniform within each region, streaklines are curved, and material lines are curved, as evidenced by the curved front of the streaklines. In FIG. 7B, compatibility is satisfied. In FIG. 7C, compatibility is not satisfied because the permeability ratio is twice that required by Eq. 2. Streamlines and material lines are curved in the opposite direction and the speed field variation is the opposite of those in FIG. 7A. Designs satisfying the compatibility conditions navigate an algebraically tractable subset of general conduction. However, FIGS. 7A and C, also show that even relatively large deviations from the compatibility condition produce relatively small amount of degradation in the velocity flow-field. Therefore, the amount of flow degradation which is acceptable in a "real" system is controlled by controlling the amount of deviation permitted from ideal compatibility, leading to practical tolerance limits with which to design these systems.

Critical Turning Angle Interfaces

FIG. 9 shows the variation of the flow velocity turning angle, $\theta_{1-\theta 2}$, of a single interface for a variety of permeability ratios, wherein the angle between the flow vector of the moving fluid in region 1 and the normal to the interface is defined as an "incident" angle of the moving fluid in region 1, and is equal to $\theta_1$. Likewise, the angle between the flow vector in region 2 (on the opposite side of the interface) and the normal to the interface in region 2 is defined as the "refracted" angle and is equal to $\theta_2$. The maximum turning angle of an interface, or "critical turning angle", $\theta_c$, is therefore, $$\theta_c \equiv \max(\theta_1 - \theta_2) = 2\tan^{-1}\left(\sqrt{\frac{\sigma_1}{\sigma_2}}\right) - \frac{\pi}{2} \quad (14)$$

and occurs at the angles $$\theta_1 = \tan^{-1}\left(\sqrt{\frac{\sigma_1}{\sigma_2}}\right), \quad (15a)$$

and $$\theta_2 = \tan^{-1}\left(\sqrt{\frac{\sigma_2}{\sigma_1}}\right). \quad (15b)$$

FIG. 10 shows the variation of these angles with the ratio of permeabilities across the interface. The permeability ratio at the critical turning angle, $\theta_c$, is from Eq. 14, $$\left.\frac{\sigma_1}{\sigma_2}\right|_c = \tan^2\left(\frac{\pi}{4} + \frac{\theta_c}{2}\right). \quad (16)$$

For example, to achieve turning angles of 30°, 45°, and 60° across a single interface, the permeability ratio $\sigma_1/\sigma_2$ must respectively be at least 3, ~5.828427, and ~13.92820. The maximum turning angle asymptotes to 90° as $\sigma_1/\sigma_2 \to \infty$. FIG. 11A shows a design and simulation of the flow at an inclined interface designed to produce a 45° turn in the flow velocity angle at this maximum turning angle condition. A 90° turn can be constructed by a sequence of two such turns "back-to-back," as shown in FIG. 11B or a channel offset with no turning can be constructed by sequencing the turns in the alternate arrangement shown in FIG. 11C.

The use of maximum turning interfaces is advantageous because they minimize the sensitivity of the interface operation to angular or permeability-ratio errors and minimize the required permeability ratio. However, sequences of interfaces designed at the maximum turning angle in a bi-permeability system cannot change the flow-channel width at either permeability and cannot generally compensate for rotation of material lines across the interface, related to hydrodynamic dispersion. Subcritical turning interfaces provide the design flexibility lacked by the critical interfaces at the cost of additional sensitivity to fabrication errors.

Subcritical Turning Angle Interfaces

Figure 12B:
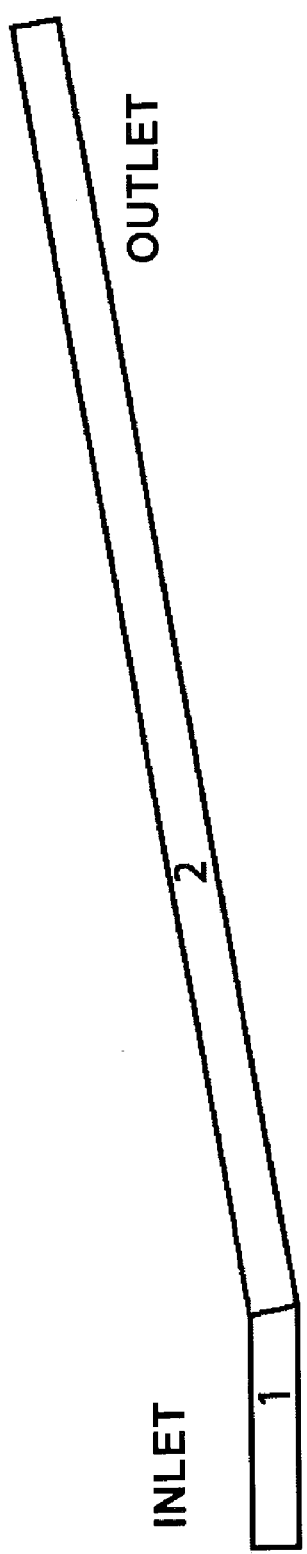
Figure 12C:
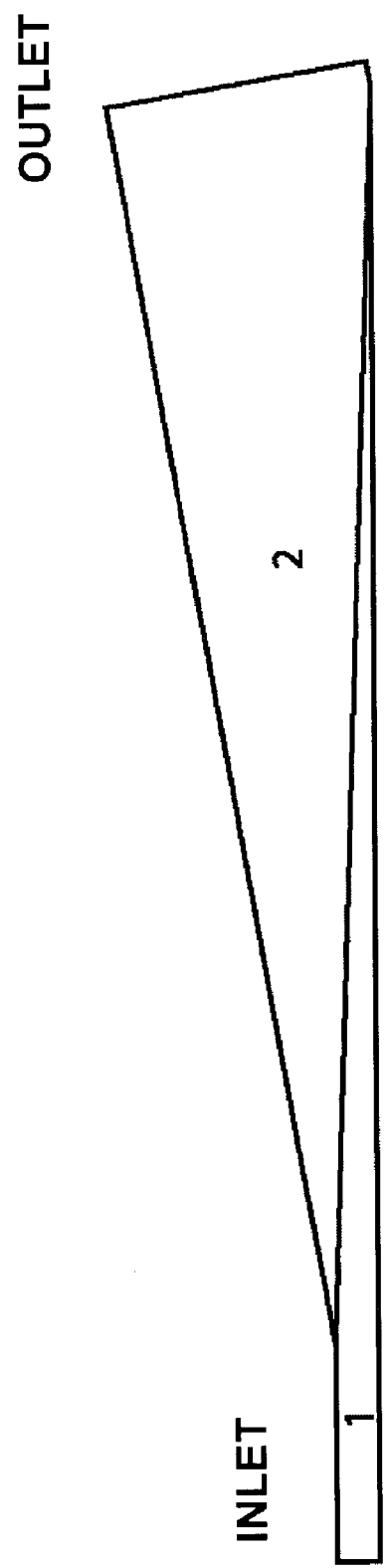
Figures 12D, 12E:
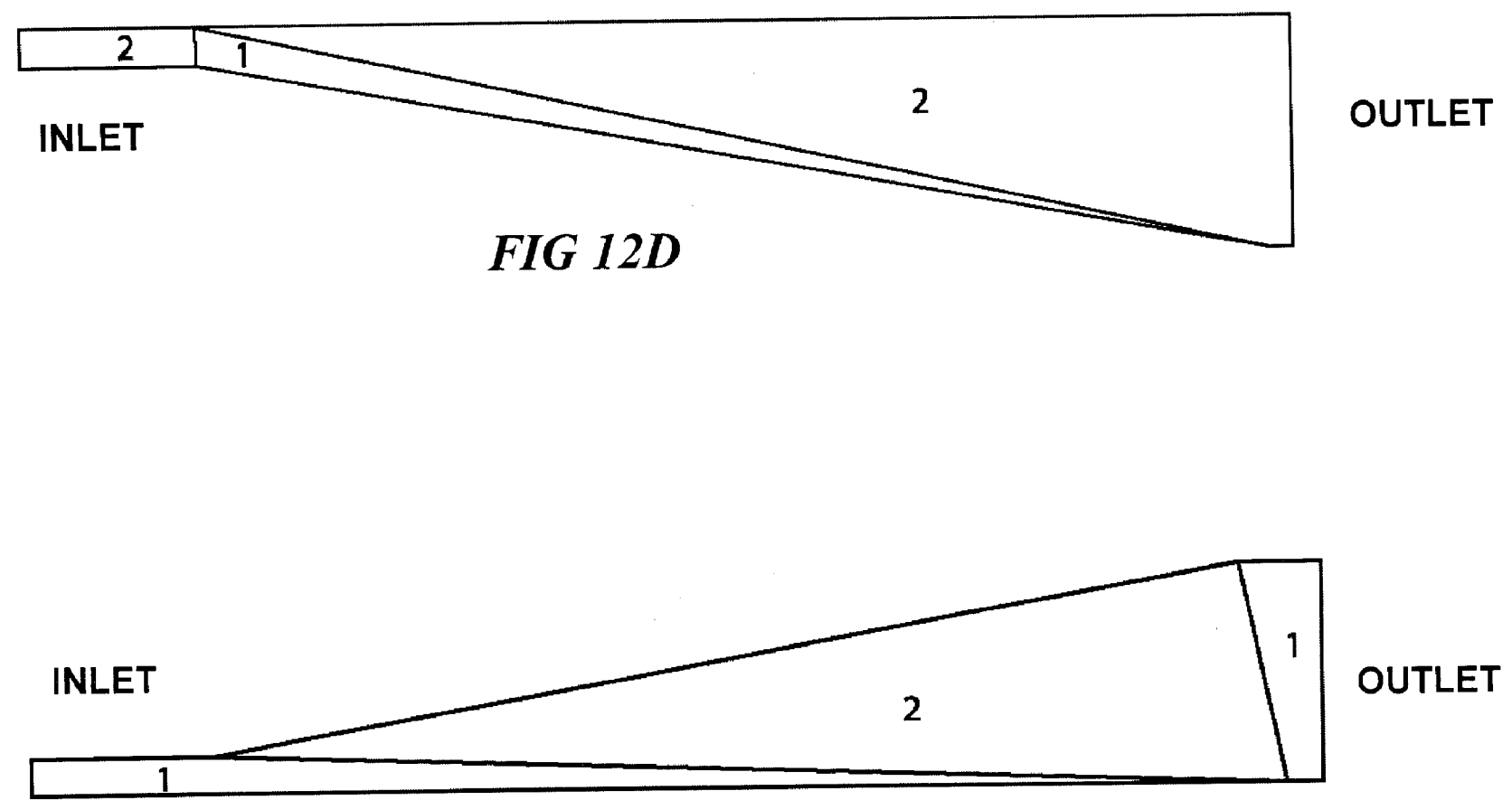

Any turning angle less than the maximum turning angle can be obtained at two different incidence-angles. One may use this additional freedom to design interfaces to widen flow-channels with or without rotation or to design interfaces which do not rotate material lines with respect to the flow. FIG. 12 compares designs of two subcritical interfaces (FIG. 12B and FIG. 12C.) that turn the flow by 10° to the critical design (FIG. 12A) that turns the flow by 45°. The ratios of the channel widths across the interfaces are different for the two angles. Thus, one may construct a device to widen or narrow a flow-channel without rotation by sequencing these two interfaces back-to-back, as shown in FIGS. 12D and 12E. FIG. 13 shows the variation in the channel width ratio across an interface, $w_2/w_1$, with the incidence-angle, $\theta_1$, at various permeability ratios. The width ratio is larger for the high-$\theta_1$ interface than the low-$\theta_1$ interface, especially at large permeability ratio. The width ratio asymptotes to unity as $\theta_1 \to 0$ and $\sigma_1/\sigma_2$ as $\theta_1 \to 90°$. The expansion or contraction ratio of a device having back-to-back interfaces is equal to the quotient of the width ratios at the larger and smaller incidence-angles, thus the channel expansion ratio for a bi-permeability, two-interface device is bounded by the permeability ratio. FIG. 14 shows a parametric plot of the turning angle versus the channel width ratio at various permeability ratios, an alternative view of the curves shown in FIGS. 9 and 13 that is useful for device design. Multiple devices can be staged to produce any desired expansion ratio and/or turning angle.

Skew-Compensated Interface Pairs

The use of subcritical interfaces likewise permits the design of interface sequences that rotate and stretch material lines by a prescribed amount. A common design goal is a device that produces no net rotation, or "skew," of material lines with respect to the flow direction.

The angles $\psi_1$ and $\psi_2$ between the normal to a material line and the flow direction in the regions 1 and 2 before and after an interface, respectively, are related by:

$$\tan\psi_2 = \left(\frac{\sigma_1}{\sigma_2}\right)\cos^2\theta_1\left[\tan\psi_1 + \tan\theta_1\left(1 - \left(\frac{\sigma_1}{\sigma_2}\right)^2(1 - \tan\psi_1\tan\theta_1)\right)\right]. \quad (17)$$

If the material line is initially perpendicular to the flow direction, $\psi_1 = 0$ and Eq. 5 simplifies to:

$$\tan\psi_2|_{\psi_1=0} = \left(\frac{\sigma_1}{\sigma_2} - \frac{\sigma_2}{\sigma_1}\right)\frac{\sin 2\theta_1}{2}, \quad (18)$$

which is plotted in FIG. 15.

Eq. 18 and FIG. 15 indicate any single, non-trivial interface having a non-zero incidence-angle skews material lines with respect to the flow. The critical incidence-angle for rotating initially normal material lines is 45° regardless of the permeability ratio. Eq. 18 is symmetrical about this critical angle, so back-to-back interfaces having incidence-angles that sum to 90° can be used to compensate for interface-induced skew or rotation of material lines. The turning angle $\theta$ of such a skew-compensated turn is:

$$\theta_T = \frac{\pi}{2} - 2\theta_1 + \tan^{-1}\left(\frac{\sigma_2}{\sigma_1}\tan\theta_1\right) - \tan^{-1}\left(\frac{\sigma_2}{\sigma_1}\frac{1}{\tan\theta_1}\right). \quad (19)$$

The geometric layout used to obtain Eq. 19 is considered further in the discussion of the Best Mode for computing the layout. FIG. 16 shows a plot of Eq. 19, the turning angle versus incidence-angle for skew-compensated interface pairs at various permeability ratios. The peak of these curves is the maximum, skew-compensated turning angle possible with two back-to-back interfaces. Again, designing for this peak is desirable for minimizing sensitivity to fabrication problems, and minimizing the permeability ratio. Note that the permeability ratio to achieve a desired no-skew turn is twice that needed to achieve an uncompensated turn. FIG. 17 shows the expansion factor for a skew-compensated interface pair.

For example, FIG. 18A shows a simulation of a skew-compensated interface pair. The material front, as indicated by the black streaklines returns to perpendicular to the flow velocity after passing the second interface. This skew-compensated "prism" design expands or narrows the channel by a factor of ~4.6 as it turns the flow velocity 45°. The permeability ratio required for this prism is ~11.66, or about twice that for the critical interface shown in FIGS. 11A–11C. Because this prism changes the width and direction of the flow, sequences of this prism design can be plumbed to make both skew-compensated turns, as shown in FIG. 18A, FIG. 19A and FIG. 19B, expansions as shown in FIGS. 20A–D, and expanding turns, as shown in FIGS. 21A–D.

FIG. 18B shows a simulation of a device made by connecting the narrow channels from the prisms shown in FIG. 18A. This device rotates the flow by 90° without changing the channel size. As shown in FIG. 18C, an alternate turn can likewise be constructed by connecting the wide channels of the prisms. The straight section between the two prisms can be arbitrarily lengthened or shortened as shown in FIG. 19A and FIG. 19B. These figures shows two simulations of this turn design, FIG. 19A having the correct permeability ratio and FIG. 19B having a permeability ratio that is off by 5%. The operation of the turn is relatively insensitive to such errors, but the small skew and curvature of the streakline front in the off-design simulation shows how such errors can limit the device performance. If needed, additional prismatic elements can be added to the design to compensate for such effects and minimize the sensitivity of the system to permeability errors. FIG. 20 shows the same prism design arranged so the entry and exit channels are parallel and each prism expands the flow-channel. The resulting expansion factor is ~21. Adding a third prism results in an expansion factor of ~99, and so on. Because of the flexibility of the faceted design method, a wide range of flow-turning angles can be implemented while expanding the flow, as illustrated in FIG. 21, which contains a faceted prism design arranged to expand the flow-channel by a factor of ~21 while turning the flow by 90°, as compared to the inline expander shown in FIG. 20.

Applications

This general design methodology supports a wide variety of practical applications. It is a methodology that allows a designer to plumb together complicated microsystems with turns, expansions, and offsets. It allows a designer to skew and stretch material lines as needed. Several specific applications of these capabilities arise immediately.

Low-Dispersion Turns and Displacers:

The insertion of turns into conduction channels can introduce large amounts of dispersion. The skew-compensated turns and channel expanders described in this document can be used directly as low-dispersion turns. A methodology has been developed to create low-dispersion turns of any angle having arbitrary expansion. The limitation of these devices is the dispersion associated with the interfaces or propagation through the low-permeability medium. The relative importance of the interface dispersion diminishes for channels that are much wider than they are deep.

Low-Dispersion Splitters and Manifolds:

It is also possible to divide flow into multiple conduction channels with full skew compensation. This will be beneficial for dividing a sample and sending it to numerous separation channels (e.g., for two dimensional separation techniques). A channel of single etch depth can be used to split flow, but this generally produces considerable dispersion. Fortunately, combinations of low-dispersion turns and displacers can be used to construct simple flow splitters and manifolds. This is done by noting that any streamline can be treated as a wall forming one side of a channel in a potential flow such as electrokinesis. Placing a flow displacer against its mirror image at the location of this streamline forms a flow divider. Further details of the splitter designs are elucidated in the Best Mode discussion which follows.

By splitting the flow in this manner, any number of exit channels can be split from a single inlet channel. Splitters with 3 and 5 exit channels have been demonstrated through numerical simulation. The design method for these splitters is given in the discussion of the Best Mode for laying out these articles. With this specific construction technique, the central exit channels are wider than the edge channels, however, using the faceted design methodology it is possible to obtain exit channels having nearly any width.

Low-Dispersion Medians:

When operated in reverse, flow splitters and manifolds become low-dispersion flow combiners. Therefore, by placing splitters back-to-back, the narrow inlet can be split into multiple channels, then recombined into a narrow outlet. Here, medians formed between the flow-channels do not perturb the flow-field. Moreover, these medians can be extended to the length of the wide channel to provide structural support for wide channels. Such support is important for channels that are extremely wide and shallow (for example, 10,000-$\mu$m wide by 1-$\mu$m deep), in which warping and sagging of the structural material can change the value of the channel depth from the intended design by a significant percentage. The number of medians is one fewer than the number of manifold channels.

Skew-compensated medians can be designed using back-to-back flow splitters that expand the flow. Here, a single median results, separating two channels that are each twice as wide as the incident flow-channel. The overall expansion ratio of 64:1 is distributed between eight internal channels that are eight times wider than the inlet and exit conduction channels. Indeed, tremendous amounts of conduction channel expansion are possible using this design methodology. Further construction details are given in the discussion of the Best Mode.

It is also possible to place medians for structural support within a wide, shallow channel with little design effort if their width is comparatively small. Medians can also be added to change the permeability of a conduction channel deliberately.

Heat-Transfer Based Design Principles:

Electrokinetic flows enable the transport of fluid in small spaces using electrically-driven systems, thereby eliminating the need for pumps in a typical pressure-driven device. This can be advantageous for removing heat from microdevices, such as microchips and computer processors. Here, heat transfer can be enhanced by using shallow channels to minimize the diffusion of heat to the fluid. In addition, a shallow and wide channel increases the surface-to-volume ratio which maximizes the removal of heat to a flow. Moreover, the wide, shallow conduction channels featured in this document mate well to the planar construction of microelectronics. The flexibility of the dispersion-compensated design principles outlined in this document enable the expansion of input conduction channels to shallow and wide channels to match the geometry of the heat generation source. Most importantly, the velocity field remains constant in the flow sections, simplifying greatly the design of such systems and eliminating the presence of unintended stagnation regions that will result from attempts at expansion of electrokinetic flow-channels by other means.

Heat generation and removal are important considerations for electrochromatographic separation techniques, where the maximum driving current results in the minimum time to perform the desired separation. The current is limited by joule heating that causes boiling of the channel fluid. The dispersion-compensating design techniques provide considerable design flexibility when considering the construction of turns, splitters and expansions for electrochromatography.

Enhanced Line-of-Sight Absorption Cell Design:

The use of line-of-sight optical absorption in microsystems has advantages over techniques such as fluorescence detection. For example, absorption is quantitative and does not require the use of molecular fluorescence labeling to obtain a signal—a major drawback for fluorescence-based detectors. Nevertheless, optical absorption-based detection is unfavorable in many microsystems because of the short path lengths over which absorption occurs, with pathlengths as short as tens of microns. The design methodology described in this document allows one to stretch material lines of the fluid by orders of magnitude by flowing across one or more interfaces. The material lines remain linear so sighting an illumination source and light collector/detector directly along the stretched material line provides a dramatic enhancement of the absorption effect, with attendant increase in sensitivity. The amount of stretching can be increased further by intentionally skewing material lines. The channel design will work well with technology to deliver light on a chip, including on-chip waveguides, optical fibers, and cavity ringdown techniques.

Evanescent Optical Excitation and Detection Designs:

The use of evanescent delivery of light to a channel for optical detection is an attractive option for chip-based systems. The low-dispersion interface design principles are ideal for evanescent techniques because the possibility of achieving extremely wide, narrow channels. In conventional conduction channels with aspect ratios near unity, most of the sample would pass undetected beneath the evanescent waves. The use of low-dispersion turns enables practical design of shallow channels that distributes analytes close to the interface where evanescent light delivery takes place. Evanescent methods will work for many techniques, such as fluorescence, absorption, and cavity-ringdown based detection. Moreover, because the analyte is delivered near the walls of the channel, any technique for optical detection in which light is propagated along a surface will be appropriate, such as the use of surface plasmon techniques.

Open-Channel Capillary CEC or HPLCC:

Capillary electrochromatographic (CEC) and high-pressure liquid chromatographic (HPLC) separations require analytes to approach an equilibrium partitioning between the mobile and stationary phase. The time to diffuse between these phases limits the approach to equilibrium and consequently the separation performance. Moreover, the analyte capacity of the system is a function of the surface-to-volume ratio. A wide, shallow, unpacked rectangular channel is an optimal configuration for such a separation system, but has not been employed in part because of the difficulty of handling injection into such a channel and detection following such a channel. The design methodology presented here provides a direct method of converting between narrow channels suitable for injection and fluorescence detection and the wide channels suitable for separation.

The simplest arrangement for this application could be a single interface pair. The first interface is operated at a large incidence-angle and expands the flow directly into the separation column. Material lines are stretched and skewed, but diffusion across the channel is relatively slow, limiting the impact on separation efficiency. At the end of the separation column, the interface is repeated, rotated by 180°. This interface removes the stretch and skew and reduces the channel width to support, for example, fluorescence detection. This arrangement has the advantage of simplicity and minimal dispersion caused by the interfaces.

An alternative arrangement could employ additional interfaces to remove the skew, increase the channel width more than is practical with a single interface, and/or reduce the sensitivity to fabrication tolerances. The cost of these extra interfaces is additional hydrodynamic dispersion at the interfaces.

A novel design methodology has been developed for flows that satisfy or approximately satisfy the Laplace equation and can therefore be viewed mathematically like conduction. Most of the emphasis in this disclosure is oriented toward microfluidic design, particularly for electrokinetic systems. For example, the emphasis on compensating for skew of material lines is intended to extend the utility of the methodology to systems that must transport analytes with minimal hydrodynamic dispersion. The same methodology can be used for electrical and thermal conductor and Darcy's law flow system design.

The methodology permits one to design these devices using a calculator rather than a simulation code. Moreover, the designs are completely uncoupled: the interfaces are immune to the details of what passes before or after, so long as their compatibility conditions are locally satisfied. This allows complex systems to be plumbed together from simpler subsystems, e.g., a 256:1 low-dispersion channel expander can be pieced together simply once a 4:1 low-dispersion prism is designed.

BEST MODE

Design Method for Providing Flow Channels with Low Dispersion Turns

To obtain the result of Eq. 7, consider the geometry given in FIG. 22A, which is similar to the diagram of FIG. 5. In FIG. 22A, channel walls 2201 and 2202 are drawn using heavy dark lines, while lighter dashed lines denote construction lines 2203a, b and 2204a, b, which are drawn parallel to, and extend each of the channel wall. Construction line 2205 is drawn parallel to interface h, and lines 2206, 2207, and 2208 are drawn perpendicular to interface h, and channel walls 2202 and 2201, respectively. One can see immediately that construction lines 2205 and 2206 form a cross, which is rotated by both $\theta_1$ and $\theta_2$ with respect to the interface, h. The resulting rotated constructions lines form a set of triangles defined by the intersection of lines 2205, 2207, and 2204b, and by the intersection of lines 2205, 2208, and 2204b. These triangles are expanded and shown in FIG. 22B, to show the length of the interface, h, the widths of the channels, $w_1$, and $w_2$, and the angles $\theta_1$, and $\theta_2$. Since both triangles share a common length h as their hypotenuse, the formula of Eq. 7 follows directly.

The geometry of FIGS. 23A and 23B is useful in helping to illustrate the derivation of Eq. 17. Here, channel walls 2301 and 2302 are again given as solid lines, while dashed lines 2303a–e represent a set of material lines propagating through the channel sections and which have a steeper angle in the second section, corresponding to a region of lower permeability, $\sigma_2$, with respect to that of the inlet region, $\sigma_1$. The material angles, $\psi_1$, and $\psi_2$, are given as the angle between the normal to the material line and the respective channel walls. If a material line is monitored as is passes through a distance $Z_1$ before the interface, h, and a distance $Z_2$ after the interface, the two triangles shown in FIG. 23B are obtained. Since the triangles share the channel interface, h, as their common side, it follows that $$\alpha_1 = \psi_1 + \theta_1 \tag{28a}$$

and, $$\alpha_2 = \psi_2 + \theta_2 \tag{28b}$$

leading indirectly to the result of Eq. 17.

The concept of the overall flow-turning angle for a two-interface turn is illustrated in FIG. 24A. The channel walls 2401–2403, and interfaces 2304 and 2305 are shown as solid lines. Lighter dashed construction lines 2306, 2307, and 2308 are drawn parallel to the upper channel walls for each of the three sections 1 through 3. The turning angle for an interface is defined as the angle from the extension of a channel to the wall of the following channel, denoted by $\theta_{T1}$ for the turning angle of the interface between sections 1 and 2 and $\theta_{T2}$ for the turning angle of the interface between sections 2 and 3. Similarly, the overall turning angle can be defined as the angle from the extension of the first section wall to the extension of the last section, $\theta_T$. Note that this definition can be applied for a system with more than two interfaces. With these definitions, it is trivial to show that the turning angles between individual sections are given by:

$$\theta_{T1} = \theta_{11} - \theta_{12}, \tag{29}$$

and, $$\theta_{T2} = \theta_{21} - \theta_{22}, \tag{30}$$

where, in generalized notation, $\theta_{n1}$ and $\theta_{n2}$ are the respective incident and exit angles for the $n^{th}$ interface. The triangle shown in FIG. 24B is formed by the intersection of the three light construction lines 2306, 2307, and 2308 shown in FIG. 24A. Here, it is clear that the overall turning angle is given by:

$$\theta_T = \theta_{T1} + \theta_{T2}, \tag{31}$$

and the application of Eqs. 29–31 above, result directly in Eq. 19.

The construction of skew-compensated interfaces using the methodology described in this document is surprisingly simple using popular CAD software. This is demonstrated in FIG. 25, wherein a three-interface expander with a permeability ratio of 10 and an incidence-angle of 85° is designed.

In FIG. 25A two parallel construction lines 1 and 2 are drawn and in FIG. 25B a third construction line 3 is drawn perpendicular to the lines of FIG. 25A. As shown in FIG. 25C, line 3 is rotated by the incident angle $\theta_{11}$ for a first interface. In FIG. 25D, a solid closed polyline 2501 is used to construct an irregular trapezoidal first region i, bounded by lines 1, 2, and 3, and which will have a permeability, $\sigma_1$.

In FIG. 25E, line 3 is now deleted and lines 1 and 2 rotated by the desired turning angle $\theta_{T1}$, for the first interface. Construction line 4 is then drawn perpendicular to lines 1 and 2, as shown in FIG. 25F. This step is followed by rotating line 4 by the incident angle $\theta_{21}$, for a second interface, as shown in FIG. 25G. In FIG. 25H, a second solid closed polyline 2502 is now used to construct a second irregular trapezoidal region ii, bounded by rotated lines 1, 2, and by the side of region i corresponding to deleted line 3. This region of the device will have a permeability, $\sigma_2$.

As shown in FIG. 25I, line 4 is now deleted, just as line 3 was in FIG. 25E, and rotated lines 1 and 2 are rotated a second time by the turning angle $\theta_{T2}$, for the second interface. Construction line 5 is drawn perpendicular to lines 1 and 2, as shown in FIG. 25J, and in FIG. 25K line 5 is rotated by the incidence-angle $\theta_{31}$, of a third interface. A third region iii, is constructed, as shown in FIG. 25L, by closing the region bounded by lines 1, 2 and 5 and the side of region ii corresponding to deleted line 4, with a third solid closed polyline 2503 forming a third irregular trapezoidal region.

Lines 1 and 2 are now rotated a third time by the turning angle $\theta_{T3}$, for the third interface as shown in FIG. 25M. If a three-interface expansion to a shallow and wide channel is desired, then lines 1 and 2 will form the walls of that channel, and the design is essentially complete.

If it is desirable to shrink the channel back to the original width of the incident conduction channel, however, the design is continued as shown in FIG. 25N by simply copying the structure shown in FIG. 25M; i.e., regions i, ii, and iii, to a location along the wide channel formed by lines 1 and 2, and rotating the structure by 180°. The resulting midsection region vi, bounded by the thrice rotated lines 1 and 2 and by the normal and inverted regions iii is enclosed with a fourth solid closed polyline 2504, connecting the two structures. The resulting finished design is shown in FIG. 25O, where inverted regions i, ii, and iii, are renamed vii, vi, and v respectively, and where regions i, iii, v, and vii have a permeability of $\sigma_1$, and regions ii, iv, and vi have a permeability of $\sigma_2$.

Figure 26A:
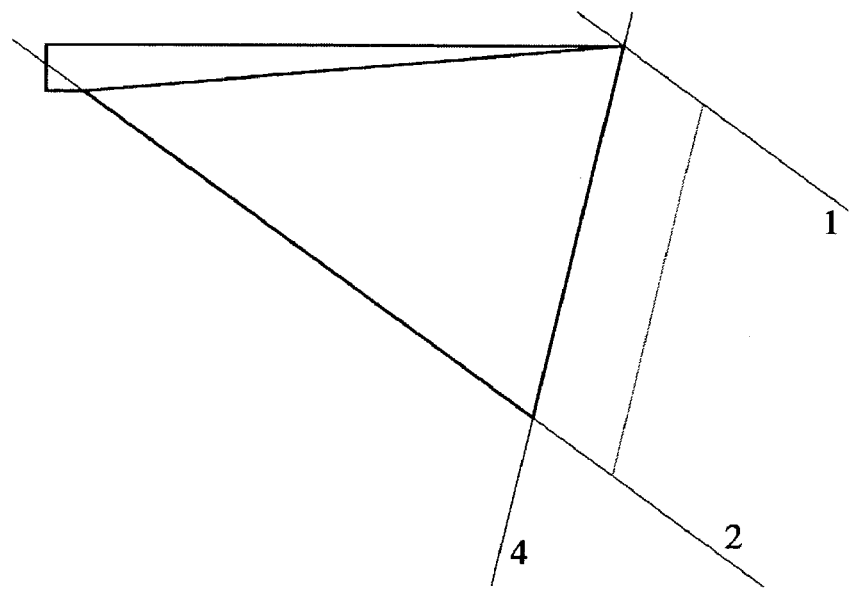

It is important to note that the length of each region can be chosen to be any value so long as the resulting regions do not overlap. For separations, for example, region iv shown in FIG. 25O would likely be comparatively long. The length is adjusted by moving the interface along the walls formed by lines 1 and 2, in each respective region, as demonstrated in FIG. 26A, which is taken from FIG. 25H with the corresponding location of the second interface represented by a line parallel to line 4. In FIG. 26A, line 4 is shifted to the apex of region i to shrink the second region ii, such that it now forms a triangular section of minimum length. It is not possible to design a relative length for the second region ii that is shorter.

Figure 26B:
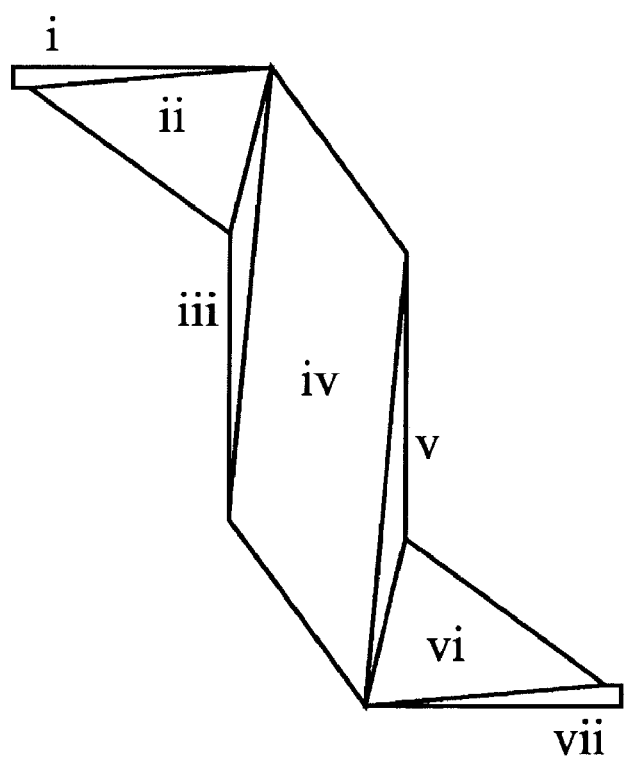

If this process is repeated for each of FIGS. 25A through 25N then the lower finalized design of FIG. 26B is obtained. Sections ii, iii, v and vi have each been reduced in length to their minimum relative values. Note that the length of section iv has no such minimum value, although here, for illustrative purposes, the length has been reduced substantially from that for FIG. 25O.

Figure 27A:
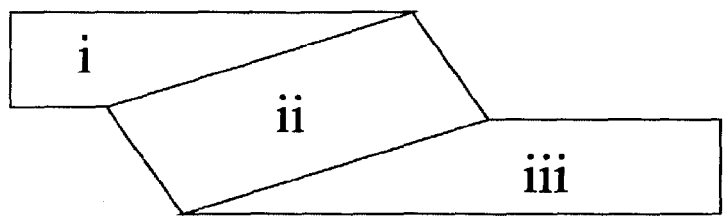
Figure 27B:
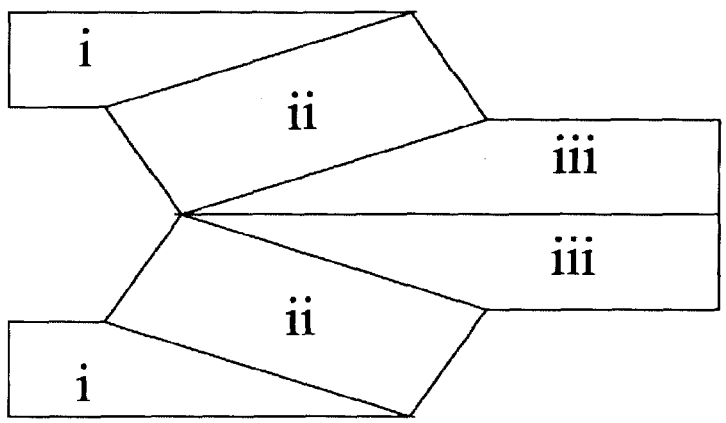
Figure 27C:
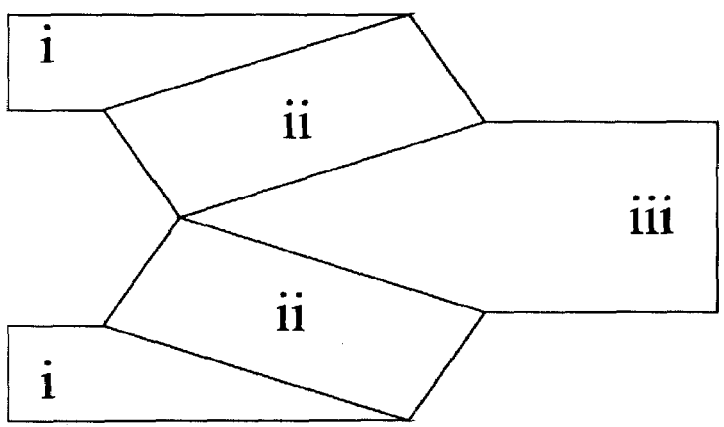

Construction of flow splitters is also remarkably simple. As illustrated in FIGS. 27A through 27I a two-way splitter and then a three-way splitter are designed based on the displacer shown in FIG. 27A. Regions i and iii represent regions of permeability $\sigma_1$ while region ii represents a region of permeability $\sigma_2$. In FIG. 27B, the displacer is copied and pasted, and then mirrored (also called "flipped" in some common drawing software). The original and mirrored displacers are aligned as shown in FIG. 27B. The two regions labeled "iii" are then merged within a single closed region as shown in FIG. 27C to provide the final design for a two-way splitter.

Figure 27D:
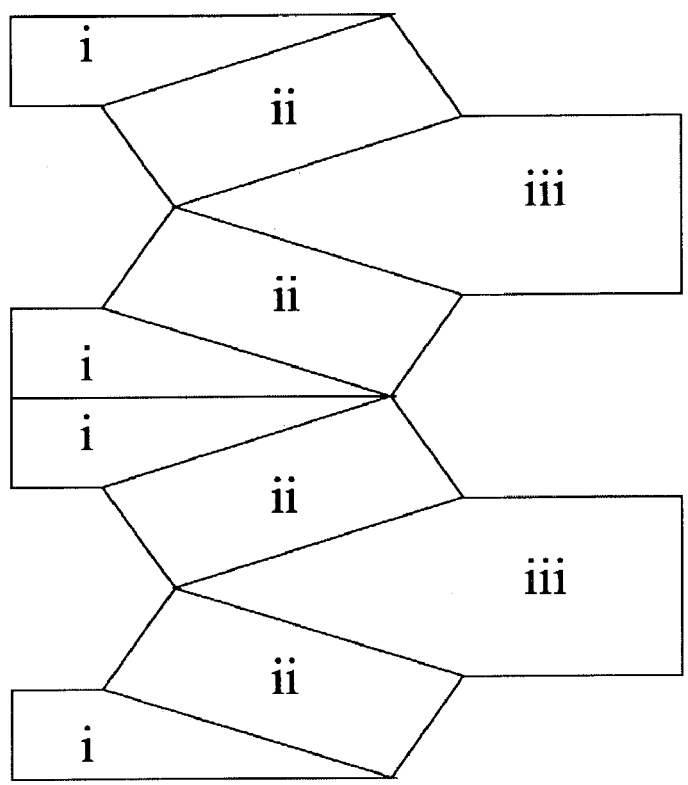
Figure 27E:
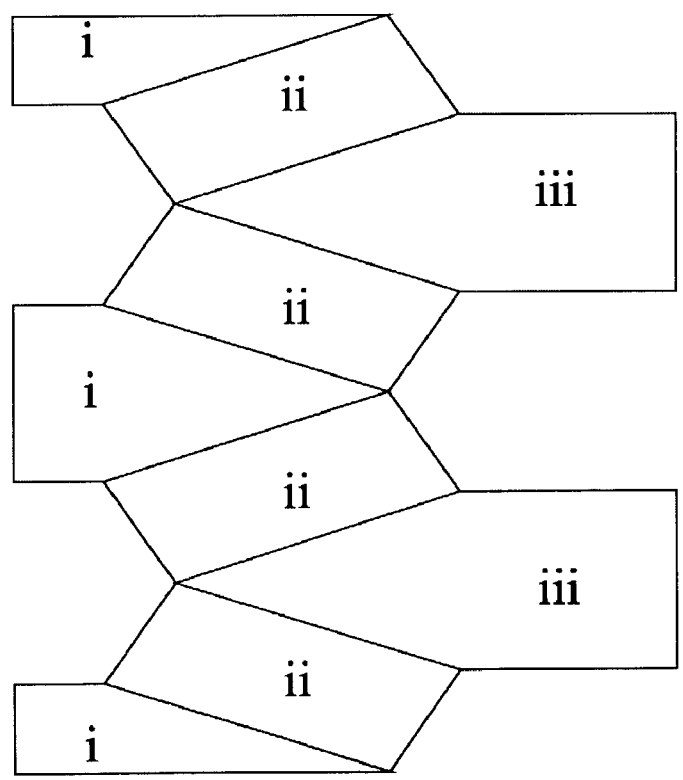
Figure 27F:
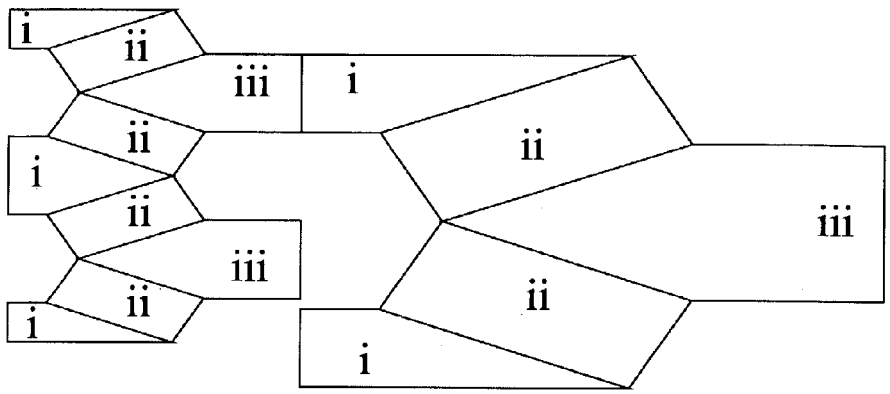

To obtain a three-way flow splitter, the design shown in FIG. 27C is copied and pasted as shown in FIG. 27D, resulting in two neighboring central regions labeled "i." These neighboring regions are again merged to form a single closed region as shown in FIG. 27E. The structure of FIG. 27C is again copied and pasted as shown in FIG. 27F. Unfortunately, the relative proportions of the structure FIG. 27C do not match the proportions of the structure of FIG. 27E, and some modification of the resultant structure is required.

Figure 27G:
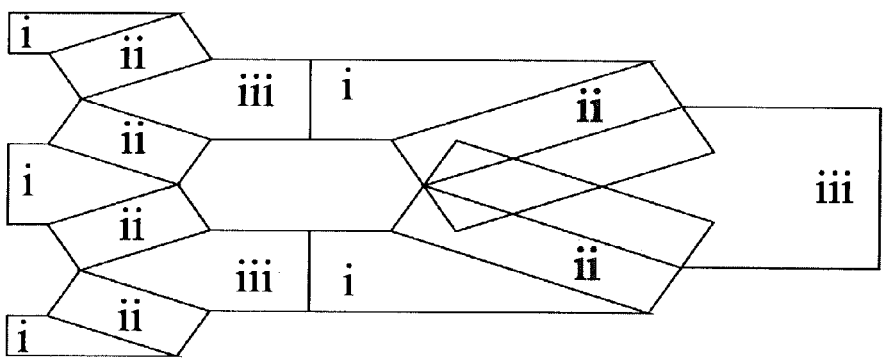
Figure 27H:
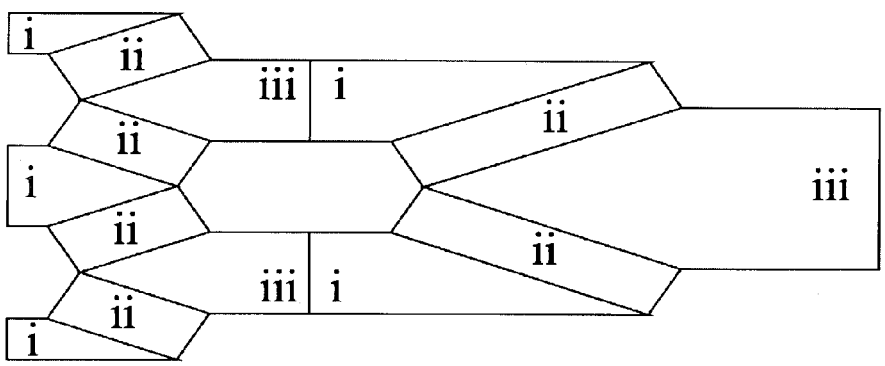
Figure 27I:
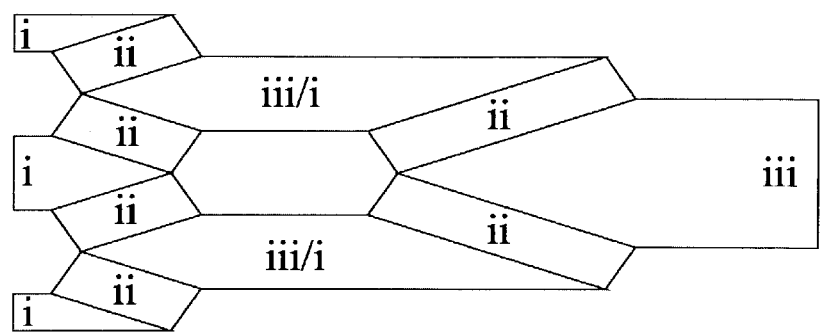

As shown in FIG. 27G, the two exit regions of the FIG. 27C structure (labeled "i") are aligned with the two regions labeled "iii" on the structure of FIG. 27E. As is readily apparent, the two regions of the FIG. 27C structure labeled "ii" are, consequently, too large and overlap region iii of that structure. These regions are therefore "shrunk-to-fit" by reducing the width of each resulting in the structure shown in FIG. 27H. Lastly, the neighboring regions iii and i are combined to provide individual closed regions resulting in the three-way flow splitter shown in FIG. 27I.

What is claimed is:

1. A flow channel, comprising:

a plurality of connected channel regions, each of said channel regions comprising a longitudinal axis, a top surface substantially parallel to a bottom surface, and first and second side walls each aligned substantially parallel to said longitudinal axis;

adjacent first and second channel regions intersecting at a first intersection plane, wherein said first and second side walls of said respective first and second channel regions meet at said first intersection plane, and wherein a normal to said first intersection plane is oriented at an angle, $\theta_{11}$, with respect to said longitudinal axis of said first channel region, and oriented at an angle, $\theta_{12}$, with respect to the longitudinal axis of said second channel region; and means for establishing a first channel permeability, $\sigma_{a1}$, in said first channel region, wherein $0.75\sigma_1 < \sigma_{a1} < 1.25\sigma_1$, and means for establishing a second channel permeability, $\sigma_{a2}$, in said second channel region, wherein $0.75\sigma_2 < \sigma_{a2} < 1.25\sigma_2$, where $\sigma_1$ and $\sigma_2$ are first and second predetermined design permeabilities related by a compatibility condition comprising $$\frac{\tan\theta_{11}}{\sigma_1} = \frac{\tan\theta_{12}}{\sigma_2},$$

wherein a fluid flowing from said first channel region into said second channel region and comprising a flux that is substantially uniform in said first channel region remains substantially uniform in said second channel region.

2. The flow channel of claim 1, wherein said fluid is turned through a first turning angle, $\theta_{T1}$, wherein $\theta_{T1}=\theta_{11}-\theta_{12}$.

3. The flow channel of claim 1, wherein a flow velocity and time-of-flight of said fluid is changed.

4. The flow channel of claim 1, further including providing first and second channel widths $w_1$ and $w_2$, wherein $$w_2 = w_1\left(\frac{\cos\theta_{12}}{\cos\theta_{11}}\right).$$

5. The flow channel of claim 1, wherein said fluid flow is represented by a series of fluid material lines, and wherein said material lines are rotated and deformed as said fluid moves through said first intersection plane.

6. The flow channel of claim 1, wherein said means for establishing said first and second channel permeabilities comprises providing a secondary structure within either or both of said first and second channel regions.

7. The flow channel of claim 6, wherein said secondary structure is selected from the list of structures consisting of a reduced channel depth, a patterned array of posts, an array of channel aligned vanes, a porous medium, and combinations thereof.

8. The flow channel of claim 2, wherein said $\theta_{T1}$ has a value less than a critical turn angle, $\theta_{C1}$, wherein $$\theta_{C1} = 2\tan^{-1}\left(\sqrt{\frac{\sigma_1}{\sigma_2}}\right) - \frac{\pi}{2}.$$

9. The flow channel of claim 2, wherein $\theta_{T1}=\theta_{C1}$.

10. The flow channel of claim 1, wherein one of said first or said second side walls of either or both of said first and second channel regions is reduced to a zero length to provide a generally triangular channel region.

11. The flow channel of claim 1, further comprising:
a third channel region intersecting said second channel regions at a second intersection plane, wherein said first and second side walls of said respective second and third channel regions meet at said second intersection plane, and wherein a normal to said second intersection plane is oriented at an angle, $\theta_{21}$, with respect to said longitudinal axis of said second channel region, and oriented at an angle, $\theta_{22}$, with respect to the longitudinal axis of said third channel region; and
means for establishing a third channel permeability, $\theta_{a3}$, in said third channel region, wherein $0.75\sigma_3<\sigma_{a3}<1.25\sigma_3$, where $\sigma_3$, is a third predetermined design permeability related to said second predetermined design permeability by a compatibility condition comprising $$\frac{\tan\theta_{21}}{\sigma_2} = \frac{\tan\theta_{22}}{\sigma_3},$$

wherein a fluid flowing from said second channel region into said third channel region and comprising a flux that is substantially uniform in said second channel region remains substantially uniform in said third channel region.

12. The flow channel of claim 11, wherein said fluid is turned through a second turning angle, $\theta_{T2}$, wherein $\theta_{T2}=\theta_{21}-\theta_{22}$.

13. The flow channel of claim 11, wherein a flow velocity and time-of-flight of said fluid is changed.

14. The flow channel of claim 11, further including providing a third channel width, $w_3$, wherein $$w_3 = w_2\left(\frac{\cos\theta_{22}}{\cos\theta_{21}}\right).$$

15. The flow channel of claim 11, wherein said fluid flow is represented by a series of fluid material lines, and wherein said material lines are rotated and deformed as said fluid moves through said second intersection plane.

16. The flow channel of claim 11, wherein said means for establishing said third channel permeability comprises providing a secondary structure within said third channel region.

17. The flow channel of claim 16, wherein said secondary structure is selected from the list of structures consisting of a reduced channel depth, a patterned array of posts, an array of channel aligned vanes, a porous medium, and combinations thereof.

18. The flow channel of claim 12, wherein said $\theta_{T2}$ has a value less than a critical turn angle, $\theta C_2$, wherein $$\theta_{C2} = 2\tan^{-1}\left(\sqrt{\frac{\sigma_2}{\sigma_3}}\right) - \frac{\pi}{2}.$$

19. The flow channel of claim 12, wherein $\theta_{T2}=\theta_{C2}$.

20. The flow channel of claim 11, wherein one of said first or said second side walls of either or both of said second and third channel regions is reduced to a zero length to provide a generally triangular channel region.

21. The flow channel 1, further comprising:
an $(n+1)^{th}$ channel region intersecting an $n^{th}$ channel region at an $n^{th}$ intersection plane, wherein said first and second side walls of said respective $n^{th}$ and $(n+1)^{th}$ channel regions meet at said $n^{th}$ intersection plane, and wherein a normal to said $n^{th}$ intersection plane is oriented at an angle $\theta_{n1}$ with respect to said longitudinal axis of said $n^{th}$ channel region, and oriented at an angle $\theta_{n2}$ with respect to the longitudinal axis of said $(n+1)^{th}$ channel region; and
means for establishing an $n^{th}$ channel permeability, $\sigma_{an}$, in said $n^{th}$ channel region, wherein $0.75\sigma_n<\sigma_{an}<1.25\sigma_n$, and means for establishing an $(n+1)^{th}$ channel permeability, $\sigma_{a(n+1)}$, in said $(n+1)^{th}$ channel region, wherein $0.75\sigma_{n+1}<\sigma_{a(n+1)}<1.25\sigma_{n+1}$, where $\sigma_n$ and $\sigma_{n+1}$, are respective $n^{th}$ and $(n+1)^{th}$ predetermined design permeabilities related by a compatibility condition comprising $$\frac{\tan\theta_{n1}}{\sigma_n} = \frac{\tan\theta_{n2}}{\sigma_{n+1}},$$

wherein a fluid flowing from said $n^{th}$ channel region into said $(n+1)^{th}$ channel region and comprising a flux that is substantially uniform in said $n^{th}$ channel regions remains substantially uniform in said $(n+1)^{th}$ channel region.

22. The flow channel of claim 21, wherein said fluid is turned through an $n^{th}$ turning angle, $\theta_{Tn}$, wherein $\theta_{Tn} = \theta_{n1} - \theta_{n2}$.

23. The flow channel of claim 21, wherein a flow velocity and time-of-flight of said fluid is changed.

24. The flow channel of claim 22, further including providing an $(n+1)^{th}$ channel width, wherein $$w_{n+1} = w_n \left(\frac{\cos\theta_{n2}}{\cos\theta_{n1}}\right).$$

25. The flow channel of claim 21, wherein said fluid flow is represented by a series of fluid material lines, and wherein said material lines are rotated and deformed as said fluid moves through said $n^{th}$ intersection plane.

26. The flow channel of claim 21, wherein said means for establishing said $(n+1)^{th}$ channel permeability further comprises providing a secondary structure within said $(n+1)^{th}$ channel region.

27. The flow channel of claim 26, wherein said secondary structure is selected from the list of structures consisting of a reduced channel depth, a patterned array of posts, an array of channel aligned vanes, a porous medium, and combinations thereof.

28. The flow channel of claim 22, wherein said $n^{th}$ turning angle is an angle less than an $n^{th}$ critical turn angle, $\theta_{Cn}$, wherein $$\theta_{Cn} = 2\tan^{-1}\left(\sqrt{\frac{\sigma_n}{\sigma_{n+1}}}\right) - \frac{\pi}{2}.$$

29. The flow channel of claim 22, wherein $\theta_{Tn} = \theta_{Cn}$.

30. The flow channel of claim 21, wherein one of said first or said second side walls of either or both of said second and third channel regions is reduced to a length of near to provide a generally triangular channel region.

31. A skew compensated flow channel comprising the flow channel of claim 9, wherein said angles $\theta_{11}$ and $\theta_{22}$ sum to 90°, said skew compensated flow channel turning said fluid through a skew compensated turn angle, $\theta_{SCT}$, wherein, $$\theta_{SCT} = \frac{\pi}{2} - 2\theta_{11} + \tan^{-1}\left(\frac{\sigma_2}{\sigma_1}\tan\theta_{11}\right) - \tan^{-1}\left(\frac{\sigma_2}{\sigma_1}\frac{1}{\tan\theta_{11}}\right).$$

32. A skew compensated flow channel comprising the flow channel of claim 20, wherein said angles $\theta_{n1}$ and $\theta_{(n+1)2}$ sum to 90°, said skew compensated flow channel turning said fluid through a skew compensated turn angle, $\theta_{SCT_n}$, wherein, $$\theta_{SCT_n} = \frac{\pi}{2} - 2\theta_{n1} + \tan^{-1}\left(\frac{\sigma_{n+1}}{\sigma_n}\tan\theta_{n1}\right) - \tan^{-1}\left(\frac{\sigma_{n+1}}{\sigma_n}\frac{1}{\tan\theta_{n1}}\right).$$

33. A flow channel for conducting a moving fluid having a flow velocity, comprising:
   a plurality of flow channel regions each having a substantially rectangular cross section;
   at least adjacent first and second channel regions;
   means for establishing respective first and second predetermined permeabilities, $\sigma_1$ and $\sigma_2$ in said respective first and second channel regions; and
   a first planar interface separating said first and second channel regions, wherein said regions are arranged to change the direction of flow of said moving fluid across said first planar interface, wherein a compatibility condition requiring $$\frac{\tan\theta_{11}}{\sigma_1} = \frac{\tan\theta_{12}}{\sigma_2}$$

is maintained, wherein $\theta_{11}$ and $\theta_{12}$ are, respectively, acute angles incident to and exiting from said first interface, said angles formed between a normal to said first planar interface and respective flow directions in said first channel region and said second channel region.

34. The flow channel of claim 33, wherein said fluid is turned through a first turning angle, $\theta_{T1}$, wherein $\theta_{T1} = \theta_{11} - \theta_{12}$.

35. The flow channel of claim 33, wherein a flow velocity and time-of-flight of said fluid is changed.

36. The flow channel of claim 33, further providing first and second channel widths $w_1$ and $w_2$, wherein $$w_2 = w_1 \left(\frac{\cos\theta_{12}}{\cos\theta_{11}}\right)$$

37. The flow channel of claim 33, wherein said fluid flow is represented by a series of fluid material lines, and wherein said material lines are rotated and deformed as said fluid moves across said first planar interface.

38. The flow channel of claim 33, wherein said means for establishing respective first and second predetermined permeabilities comprises providing a secondary structure within either or both of said first and second channel regions.

39. The flow channel of claim 38, wherein said secondary structure is selected from the list of structures consisting of a reduced channel depth, a patterned array of posts, an array of channel aligned vanes, a porous medium, and combinations thereof.

40. The flow channel of claim 34, wherein said first turning angle $\theta_{T1}$ does not exceed a first critical turn angle $\theta_{CT1}$, wherein $$\theta_{CT1} = 2\tan^{-1}\left(\sqrt{\frac{\sigma_1}{\sigma_2}}\right) - \frac{\pi}{2}.$$

41. The flow channel of claim 34, wherein said first turning angle $\theta T1$ is equal to said first critical turn angle $\theta_{CT1}$.

42. The flow channel of claim 33, comprising:
a third channel region adjacent to said second channel region;
means for establishing a third permeability, $\sigma_3$, in said third channel region; and
a second planar interface separating said second and third channel regions, wherein said regions are arranged to change the direction of flow of said fluid moving across said second interface, wherein a compatibility condition requiring $$\frac{\tan\theta_{21}}{\sigma_2} = \frac{\tan\theta_{22}}{\sigma_3}$$

is maintained, where $\theta_{21}$ and $\theta_{22}$, are, respectively, acute angles incident to and exiting from said second interface, said angles formed between a normal to said interface and respective flow directions in said second and said third channel regions.

43. The flow channel of claim 42, wherein said fluid is turned through a second turning angle, $\theta_{T2}$, wherein $\theta_{T2}=\theta_{21}-\theta_{22}$.

44. The flow channel of claim 42, wherein a flow velocity and time-of-flight of said fluid is changed.

45. The flow channel of claim 42, further including providing a third channel width, $w_3$, wherein $$w_3 = w_2\left(\frac{\cos\theta_{22}}{\cos\theta_{21}}\right).$$

46. The flow channel of claim 42, wherein said fluid flow is represented by a series of fluid material lines, and wherein said material lines are rotated and deformed as said fluid moves across said second planar interface.

47. The flow channel of claim 42, wherein said means for establishing said third predetermined permeability comprises providing a secondary structure in said third channel region.

48. The flow channel of claim 47, wherein said secondary structure is selected from the list of structures consisting of a reduced channel depth, a patterned array of posts, an array of channel aligned vanes, a porous medium, and combinations thereof.

49. The flow channel of claim 42, wherein said second turning angle $\theta_{T2}$ does not exceed a second critical turn angle $\theta_{CT2}$, wherein $$\theta_{CT2} = 2\tan^{-1}\left(\sqrt{\frac{\sigma_2}{\sigma_3}}\right) - \frac{\pi}{2}.$$

50. The flow channel of claim 49, wherein said second turning angle $\theta_{T2}$ is equal to said second critical turn angle $\theta_{CT2}$.

51. A method for providing a flow channel, comprising:
providing a plurality of connected channel regions, wherein each of said channel regions comprises a longitudinal axis, a top surface substantially parallel to a bottom surface, and first and second side walls each aligned substantially parallel to said longitudinal axis;
providing at least adjacent first and second channel regions, said first and second channel regions intersecting at a first intersection plane, wherein said first and second side walls of said respective first and second channel regions meet at said first intersection plane, and wherein a normal to said first intersection plane is oriented at an angle, $\theta_{11}$, with respect to said longitudinal axis of said first channel region, and oriented at an angle, $\theta_{12}$, with respect to the longitudinal axis of said second channel region; and
establishing a first channel permeability, $\sigma_{a1}$, in said first channel region, wherein $0.75\sigma_1<\sigma_{a1}<1.25\sigma_1$, and means for establishing a second channel permeability, $\sigma_{a2}$, in said second channel region, wherein $0.75\sigma_2<\sigma_{a2}<1.25\sigma_2$, where $\sigma_1$ and $\sigma_2$ are first and second predetermined design permeabilities related by a compatibility condition comprising $$\frac{\tan\theta_{11}}{\sigma_1} = \frac{\tan\theta_{12}}{\sigma_2},$$

wherein a fluid flowing from said first channel region into said second channel region and comprising a flux that is substantially uniform in said first channel region remains substantially uniform in said second channel region.

52. The method of claim 51, further including turning said fluid by a first turning angle, $\theta_{T1}$, wherein $\theta_{T1}=\theta_{11}-\theta_{12}$.

53. The method of claim 51, wherein a flow velocity and time-of-flight of said fluid is changed.

54. The method of claim 51, further including providing first and second channel widths $w_1$ and $w_2$, wherein $$w_2 = w_1\left(\frac{\cos\theta_{12}}{\cos\theta_{11}}\right).$$

55. The method of claim 51, wherein said fluid flow is represented by a series of fluid material lines, and wherein said material lines are rotated and deformed as said fluid moves through said first intersection plane.

* * * * *